(12) United States Patent
Doi et al.

(10) Patent No.: US 6,525,670 B1
(45) Date of Patent: Feb. 25, 2003

(54) IN-HOME HEALTH CARE SYSTEM

(75) Inventors: Kenji Doi, Nara (JP); Mitsuhide Maeda, Osaka (JP); Hitoshi Sakakibara, Osaka (JP); Masaru Hashimoto, Osaka (JP); Keiichi Yoshida, Osaka (JP); Kazuya Kitayama, Osaka (JP); Masaki Koyama, Osaka (JP); Osamu Nishimura, Osaka (JP); Yoshiko Suzuki, Osaka (JP)

(73) Assignee: Matsushita Electric Works, Ltd., Osaka (JP)

( * ) Notice: Subject to any disclaimer, the term of this patent is extended or adjusted under 35 U.S.C. 154(b) by 0 days.

(21) Appl. No.: 09/318,017

(22) Filed: May 25, 1999

(30) Foreign Application Priority Data

| Oct. 23, 1998 | (JP) | ............................................. | 10-302934 |
| Oct. 23, 1998 | (JP) | ............................................. | 10-302935 |
| Oct. 23, 1998 | (JP) | ............................................. | 10-302937 |
| Oct. 23, 1998 | (JP) | ............................................. | 10-302938 |
| Oct. 23, 1998 | (JP) | ............................................. | 10-302939 |

(51) Int. Cl.$^7$ ................................................ G08B 21/00
(52) U.S. Cl. ..................... 340/870.16; 128/903; 600/300
(58) Field of Search ..................... 340/870.16; 128/903; 600/300, 372, 382

(56) References Cited

U.S. PATENT DOCUMENTS

| 4,974,607 A | | 12/1990 | Miwa | |
| 5,590,648 A | | 1/1997 | Mitchell et al. | |
| 5,704,366 A | | 1/1998 | Tanklind et al. | |
| 5,785,650 A | * | 7/1998 | Akasaka et al. | ............ 600/300 |
| 5,792,047 A | | 8/1998 | Coggins | |
| 5,862,803 A | * | 1/1999 | Besson et al. | .............. 128/903 |
| 5,944,659 A | * | 8/1999 | Flach et al. | .................. 600/300 |
| 6,047,203 A | * | 4/2000 | Sackner et al. | ............. 600/388 |

FOREIGN PATENT DOCUMENTS

| FR | 2 717 332 | 9/1995 |
| JP | 8-275927 | 8/1996 |
| JP | 9-140748 | 9/1997 |
| WO | 98/38909 | 9/1998 |

* cited by examiner

Primary Examiner—Timothy Edwards, Jr.
(74) Attorney, Agent, or Firm—Fish & Richardson P.C.

(57) ABSTRACT

A communication system includes a transmitting device, a receiving device having receiving device for receiving data transmitted by said transmitting device and managing device for managing received data, detecting device for detecting whether or not communication of data between said transmitting device and said receiving device is permitted, said detecting device being provided with at least one of said transmitting device and said receiving device, wherein when said detecting device detects a fact that communication of data is permitted, said transmitting device starts transmitting data to said receiving device.

46 Claims, 28 Drawing Sheets

NO CONNECTION

CONNECTED

IN-HOME HEALTH CARE SYSTEM

BACKGROUND OF INVENTION

1. Field of Invention

The present invention relates to an in-home health caring system incorporating a terminal device for central-managing data about a state of health measured in a home so that contribution to voluntary health care is made and arranged to transmit data to a remote expert, such as a doctor or a public health nurse, so as to enable health care to be performed in a home while advises are being given from the expert.

2. Related Art

Since the aging society rapidly proceeds in recent years, the state of finances of the medical expenses in Japan has a great difficulty. Therefore, countermeasures must be taken. The Japanese government has enlarged medical payments for the people. Moreover, conversion from the former basic principle of "ready detection of disease and early treatment" to "improvement in the health to prevent disease" has been given an important position.

As a means for effectively realizing the "improvement in the health to prevent disease", an "in-home health caring system" has been suggested. The system has a structure that data (for example, data about the blood pressure measured by an electronic sphygmomanometer and the body temperature measured by a clinical thermometer) about a state of the health which can be measured in a home, which is hereinafter expresses as "health data"). Measured data is transmitted to a medical facility, a medical examination center or the like through a communication network, such as the public line or the CATV line. Thus, data is analyzed/determined by an expert.

The foregoing in-home health caring system enables daily health care in a home to be performed under guidance of an expert. As a result, reliable health care can be performed, thus causing the number of attendance of a hospital to be decreased.

As a system of the foregoing type, an in-home health caring system structured as shown in FIG. 35 has been suggested in Unexamined Japanese Patent Publication Hei. 8-275927. The foregoing system incorporates each terminal device having a function to serve as a health measuring device which includes a sphygmomanometer and an electrocardiograph.

In general, a terminal device for use in the in-home health caring system must transmit data about the state of the health to a medical facility, a medical examination center or the like. Therefore, connection terminals are disposed at certain positions. If a telephone line is employed, the terminal devices are disposed adjacent to modular terminals. Therefore, the in-home health caring system shown in FIG. 1 requires a user to move to the terminal device when the state of the health of the user is measured if the terminal device and the health measuring device are integrated with each other. Therefore, the system cannot easily be used.

Therefore, an in-home health caring system disclosed in Unexamined Japanese Patent Publication Hei. 9-140748 incorporates terminal devices and health measuring devices which are individually provided. Moreover, each of the health measuring devices, such as a sphygmomanometer and a clinical thermometer, is provided with an infrared-ray communication function to enable measured data to be supplied to the terminal device from a remote position. On the other hand, when the terminal device and the health measuring device are connected to each other through a cable or the like followed by depressing a data transmitting button or the like provided for the health measuring device, an in-home health caring system of the foregoing type enables health data measured at an arbitrary position to be input to the terminal device.

The in-home health caring system having the above-mentioned structure is able to improve reliability of the health care as the number of types of health measuring devices increases. If the wireless communication function using electric waves or infrared rays is provided for all of the health measuring devices, the cost of the in-home health caring system is enlarged excessively. As a result, there arises a problem in that the introduction of the in-home health caring system is inhibited.

The foregoing system incorporates one data transferring device which has means for reading data from a health measuring device and means for wireless-transmitting read data to a terminal device to realize wireless input of data to the terminal device without enlargement of the cost.

The in-home health caring system structured such that the health measuring device and the terminal device are provided individually has a problem in that employment of a variety of communication methods between the health measuring device and the terminal device inhibits convenient operation.

Since the health measuring devices have various communication methods, a receiving means and a connection terminal adaptable to each communication method must be provided for the terminal device to receive health data transmitted from a variety of health measuring devices (for example, a health measuring device for performing synchronous serial communication method requires the terminal device to be provided with a connection terminal adaptable to the synchronous serial communication method). To enable health data to obtain health data from a plurality of health measuring devices having various communication methods, the terminal device must constitute a data receiving application adaptable to each communication method. Then, a user must select a suitable application from the applications, followed by starting transmission of health data to the terminal device. As described above, a very complicated process is required.

The in-home health caring system structured such that the health measuring device and the terminal device are provided individually has a problem in that an operation for starting input by depressing the data transmitting button must be performed whenever the health measuring device and the terminal device are connected to each other. Thus, a complicated operation must be performed by a user. To accurately recognize a state of the health of the user, a multiplicity of health measuring devices must be used. The foregoing operations become troublesome when a large number of the health measuring devices are used.

When wireless communication is employed to perform communication between the health measuring device and the terminal device, health data can be read by the terminal device only by depressing the communication start button provided for the health measuring device. Therefore, the operation for connecting cables is not required. Thus, the operation for inputting health data can easily be performed. When wireless communication of all of the health measuring devices is realized, the cost is enlarged excessively. In a case of a health measuring device which must transmit data in a great quantity, the wireless communication is not necessarily an appropriate communication method. Therefore, when only the wireless communication is employed, the type of the health measuring device is sometimes limited. Therefore, it is preferable that the wired communication and the wireless communication are selectively employed between the health measuring device and the terminal device.

In the in-home health caring system in which the wired communication and the wireless communication are employed together between the health measuring device and the terminal device, data is communicated adjacent to the terminal device when the wired communication is employed. When the wireless communication is employed, data is communicated from a position apart from the terminal device. Therefore, the wireless communication is sometimes incorrectly started even if the wired communication is being performed.

However, the terminal device of the in-home health caring system cannot simultaneously process health data transmitted from a plurality of the health measuring devices. Therefore, if health data is simultaneously transmitted from the plural health measuring devices, the terminal device cannot receive all of the health data items. Therefore, a portion of health data cannot be read by the terminal device. Therefore, a user must pay attention to prevent simultaneous transmission of health data from the plural health measuring devices. According to the circumstances, an by operation for again inputting all of the health data items which have simultaneously be transmitted is required. Thus, there arises a problem in that the system cannot easily be used.

However, the terminal device of the in-home health caring system cannot simultaneously process health data transmitted from a plurality of the health measuring devices. Therefore, if health data is simultaneously transmitted from the plural health measuring devices, the terminal device cannot receive all of the health data items. Therefore, a portion of health data cannot be read by the terminal device. Therefore, a user must pay attention to prevent simultaneous transmission of health data from the plural health measuring devices. According to the circumstances, an operation for again inputting all of the health data items which have simultaneously be transmitted is required. Thus, there arises a problem in that the system cannot easily be used.

SUMMARY OF INVENTION

In view of the foregoing, an object of the present invention is to provide a low-cost in-home health caring system which can easily be operated.

In view of the foregoing, another object of the present invention is to provide a low-cost in-home health caring system which can easily be operated and which is able to input data of a health measuring device, which cannot be read by a data transferring device, to a terminal device.

In view of the foregoing, another object of the present invention is to provide an in-home health caring system which enables communication of health data between a health measuring device and a terminal device to be performed without a necessity of recognizing a variety of communication methods employed to perform data communication between the health measuring device and the terminal device.

In view of the foregoing, another object of the present invention is to provide an in-home health caring system which is capable of facilitating a process for inputting health data to a terminal device.

An aspect of the present invention provided in an in-home health caring system comprising: a plurality of health measuring devices each having means for measuring a state of the health and means for transmitting measured data to a data transferring device; the data transferring device incorporating means for reading data transmitted by the health measuring device and means for wireless-transmitting, to a terminal device, read data; and the terminal device incorporating means for receiving data wireless-transmitted by the data transferring device, means for managing data and means arranged to be operated by a user.

Another aspect of the present invention is provided in an in-home health caring system described above, wherein the data transferring means incorporates means for identifying a user, and ID data of the person identified by the means for identifying a user is enabled to be transmitted to the terminal device.

Another aspect of the present invention is provided in an in-home health caring system in described above, wherein the data transferring means incorporates means for remote-controlling the terminal device, and a control code for remote-controlling the terminal device is enabled to be transmitted to the terminal device.

Another aspect of the present invention, there is provided an in-home health caring system comprising: a plurality of health measuring devices each having means for measuring a state of the health and means for transmitting measured data to a data transferring device; the data transferring device incorporating means for reading data transmitted by the health measuring device and means for wireless-transmitting, to a terminal device, read data; and the terminal device incorporating means for receiving data wireless-transmitted by the data transferring device, means for managing data and means arranged to be operated by a user, wherein the data transferring device is provided with means for inputting numerals, characters and graphics, and data input by the input means is enabled to be transmitted to the terminal device.

Another aspect of the present invention, there is provided an in-home health caring system an in-home health caring system comprising: a plurality of health measuring devices each having means for measuring a state of the health and means for transmitting measured data to a data transferring device; the data transferring device incorporating means for reading data transmitted by the health measuring device and means for wireless-transmitting, to a terminal device, read data; and the terminal device incorporating means for receiving data wireless-transmitted by the data transferring device, means for managing data and means arranged to be operated by a user, wherein an input device having means for inputting numerals, characters and graphics and means for wireless-transmitting supplied data to the terminal device are provided.

Another aspect of the present invention, there is provided an in-home health caring system comprising: a health measuring device incorporating measuring means for measuring a state of the health and transmitting means for transmitting measured data to a terminal device; and the terminal device incorporating receiving means for receiving data transmitted by the health measuring device and managing means for managing received data, wherein one connection terminal and determining means for determining a communication method of data received through the connection terminal are provided for the terminal device so that data transmitted from the health measuring device by using a variety of communication methods is received by the terminal device through the connection terminal.

Another aspect of the present invention, a structure according to the in-home health caring system is described above, wherein the health measuring device is arranged to transmit data after a lapse of a delay time previously determined for each communication method after the health measuring device and the terminal device have been connected to each other, and the determining means for determining the communication method of the terminal device measures time taken from establishment of the connection between the health measuring device and the terminal device to start of transmission of data to determine the communication method employed by the health measuring device.

Another aspect of the present invention, there is provided an in-home health caring system comprising: a health measuring device incorporating measuring means for measuring a state of health and transmitting means for transmitting measured data to a terminal device; and the terminal device incorporating receiving means for receiving data transmitted from the health measuring device and structured such that wired communication is performed between the health measuring device and the terminal device, wherein detecting means for detecting whether or not the wired communication is enabled is provided for at least either of the health measuring device or the terminal device, and transmission of data from the health measuring device to the terminal device is started when detection has been made that the wired communication can be performed.

Another aspect of the present invention, there is provided a structure according to the in-home health caring system described above, wherein the detecting means incorporates a circuit portion in which the logical level of a signal is inverted when the wired connection between the health measuring device and the terminal device permits communication.

Another aspect of the present invention, there is provided a structure according to the in-home health caring system described above, wherein data is transmitted from the health measuring device after a lapse of a predetermined waiting time from detection of the communication permissible state by the detecting means.

Another aspect of the present invention, there is provided a structure according to the in-home health caring system described above, wherein a signal line disposed between the health measuring device and the terminal device to transmit data is physically interrupted until the waiting time elapses.

Another aspect of the present invention, there is provided an in-home health caring system comprising: a health measuring device incorporating measuring means for measuring a state of health and transmitting means for transmitting data to a terminal device; and the terminal device incorporating receiving means for receiving data transmitted from the health measuring device and managing means for managing received data, wherein a communication control portion for performing an interruption process is provided for the terminal device, and the communication control portion performs waiting for receipt of data transmitted by wired communication or wireless communication.

Another aspect of the present invention, there is provided a structure according to the in-home health caring system described above, wherein when data transmitted by the wireless communication has been received during receipt of data by the wired communication, the communication control portion of the terminal device interrupts the receipt of data by the wired communication and data transmitted by the wireless communication is received with a priority, and then data transmitted by the wired communication is received.

Another aspect of the present invention, there is provided a structure according to the in-home health caring system described above, wherein when data transmitted by the wired communication is received during receipt of data transmitted by the wireless communication, the communication control portion of the terminal device does not interrupt receipt of data transmitted by the wireless communication and receives data transmitted by the wireless communication with a priority, and then the communication control portion receives data transmitted by the wired communication.

According to another aspect of the present invention, there is provided an in-home health caring system comprising: a health measuring device incorporating measuring means for measuring a state of health and transmitting means for transmitting measured data to a terminal device; and a terminal device incorporates receiving means for receiving data transmitted by the health measuring device and managing means for managing received data, wherein a communication control portion having a buffer function is provided for the terminal device, and when data transmitted by wireless communication or wired communication is received during receipt of data by the other communication method which is the wireless communication or the wired communication, the communication control portion temporarily stores data transmitted by the other communication method until receipt of data transmitted by the communication method which has previously been employed is completed.

According to the present invention, the necessity of performing a process for starting transmission of data after communication of data has been permitted can be eliminated. After communication of data has been permitted, transmission of data is automatically started. Therefore, a complicated operation for inputting data to the receiving device can be omitted.

According to the present invention, whether or not communication of data has been permitted can electrically be detected without a complicated structure. Therefore, a state in which communication is permitted can reliably be detected.

According to the present invention, a period of time immediately after establishment of the connection in which noise is most easily produced is made to be the waiting time in which transmission of data is inhibited. Therefore, a malfunction caused from noise produced when the transmitting device and the receiving device have been connected to each other can be prevented. As a result, reliability of data communication can be improved.

According to the present invention, the signal line for transmitting data between the transmitting device and the receiving device is physically interrupted until the waiting time elapses. Noise produced when the transmitting device and the receiving device has been connected to each other can completely be prevented. As a result, a malfunction caused from noise can be prevented.

According to the present invention, the in-home health caring system enables the necessity of previously inputting, to the terminal device, information of the health measuring device with which wired communication will be performed can be eliminated. Therefore, an effect can be obtained in that input of health data to the terminal device can furthermore be facilitated.

According to the present invention, the receiving device is able to determine a transmitting device from which data has been transmitted. Therefore, data transmitted together with the ID code can automatically be processed in accordance with the transmitting device.

According to the present invention, the communication method of data which must be transmitted from the transmitting device can automatically be determined/processed by the receiving device. If a variety of communication methods are employed to communicate data between the transmitting device and the receiving device are employed, a user does not recognize the communication method when data is communicated between the transmitting device and the receiving device.

According to the present invention, a user is not required to select a connection terminal. Therefore, the user is able to easily establish the connection to the connection terminal.

According to the present invention, the communication method can be determined only by measuring time taken from establishment of the connection between the transmitting device and the receiving device to start of transmission of data. Therefore, the communication method can easily and accurately be determined.

According to the present invention, one relay device capable of reading data of adaptable of transmitting devices is provided. Therefore, a necessity of providing means for wireless-transmitting data for all of the transmitting devices can be eliminated. Moreover, data can be wireless-transmitted from the transmitting device to the receiving device. Therefore, a low-cost communication system which can easily be operated can be provided.

According to the present invention, data of each person can be input from a remote position to the receiving device if a plurality of users use the system. Therefore, a communication system which can easily be operated can be provided.

According to the present invention, the relay device is able to remote-control the receiving device. Therefore, all of the operations of the receiving device can be performed from a remote position. Therefore, a communication system which can easily be operated can be provided.

According to the present invention, data which must be transmitted from the transmitting device and which cannot be read by the relay device can be input to the relay device by using the means for inputting numerals, characters and graphics. Therefore, a communication system can be provided with which data which cannot be read by the relay device and which has been transmitted by the transmitting device can be input to the receiving device.

According to the present invention, data which cannot be read by the relay device and which must be transmitted from the transmitting device can be wireless-transmitted to the receiving device by using the sub-input device. Therefore, data which cannot be read by the relay device and which must be transmitted by the transmitting device can be input to the receiving device by using the sub-input device. As a result, a communication system can be provided with which the relay device and the sub-input device can be disposed at an arbitrary position.

According to the present invention, data transmitted by a predetermined communication method is received with priority if an interruption process causes data to be transmitted by both of wired communication and wireless communication or if transmission of data by either of the communication method is started during receipt of data by the other communication method. Therefore, the possibility of generation of data which cannot be received can be lowered. As a result, a communication system can be provided with which a user is able to easily input data to the receiving device.

According to the present invention, data transmitted by both of the wired communication and the wireless communication can be received. Therefore, an effect can be obtained in that operability of a process for inputting data to the receiving device and the reliability of the system can be improved.

According to the present invention, data transmitted by wired communication and wireless communication can be received. Therefore, an effect can be obtained in that operability of a process for inputting data to the receiving device and the reliability of the system can be improved.

According to the present invention, the buffer function enables data transmitted by the two communication methods to simultaneously be received. Therefore, a communication system can be provided with which a user is not required to perform a complicated operation to input data to the receiving device.

BRIEF DESCRIPTION OF DRAWINGS

FIGS. 23(a) to (b) are block diagrams showing another detecting means, in which FIG. 23(a) shows a non-connection state and FIG. 23(b) shows a connection state;

DETAILED DESCRIPTION OF PREFERRED EMBODIMENTS

First Embodiment

Figure 1:
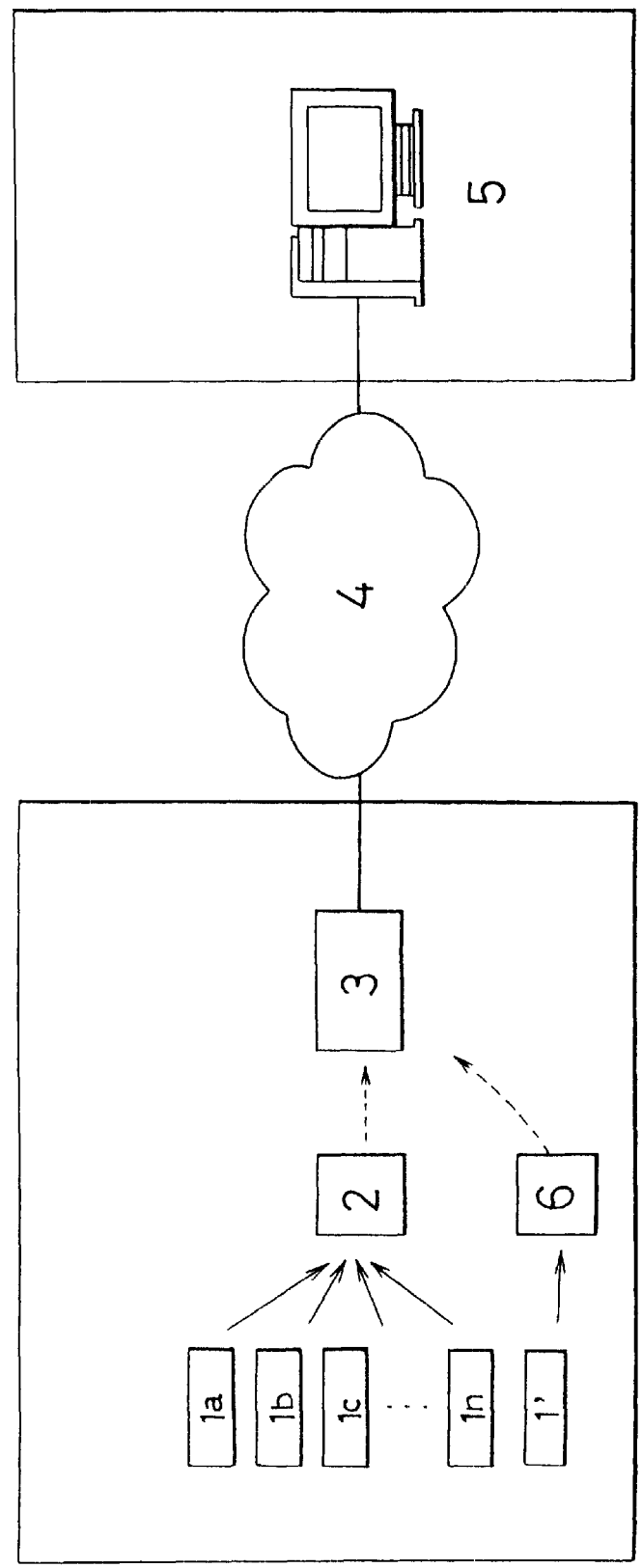
FIG. 1 is a block diagram showing an in-home health caring system according to the present invention.
Figure 2:
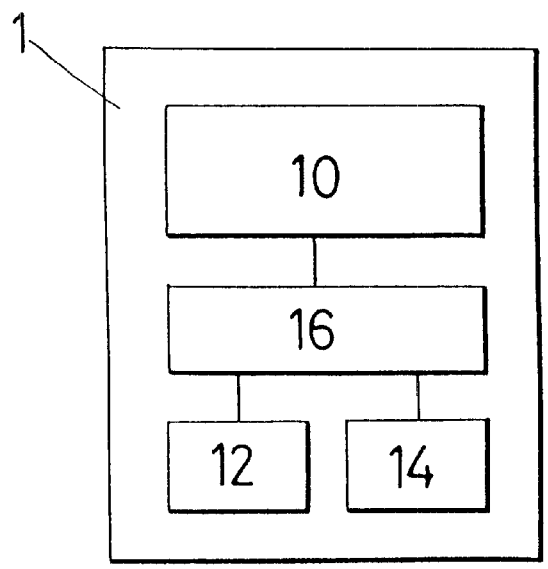
FIG. 2 is a block diagram showing the internal structure of a health measuring device.
Figure 3:
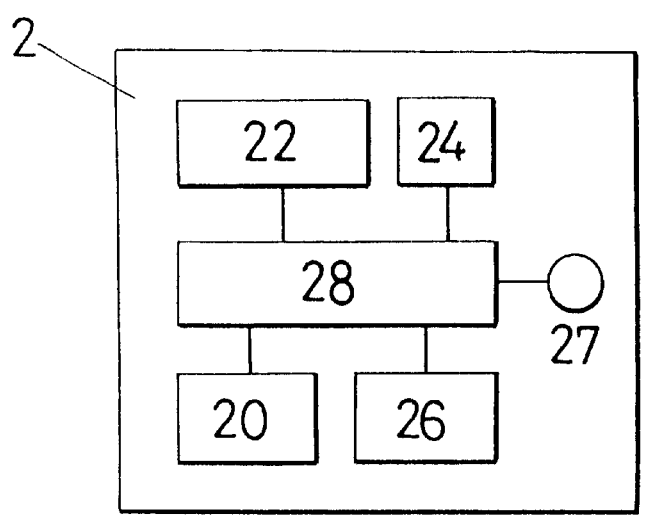
FIG. 3 is a block diagram showing the internal structure of the data transferring device.
Figure 4:
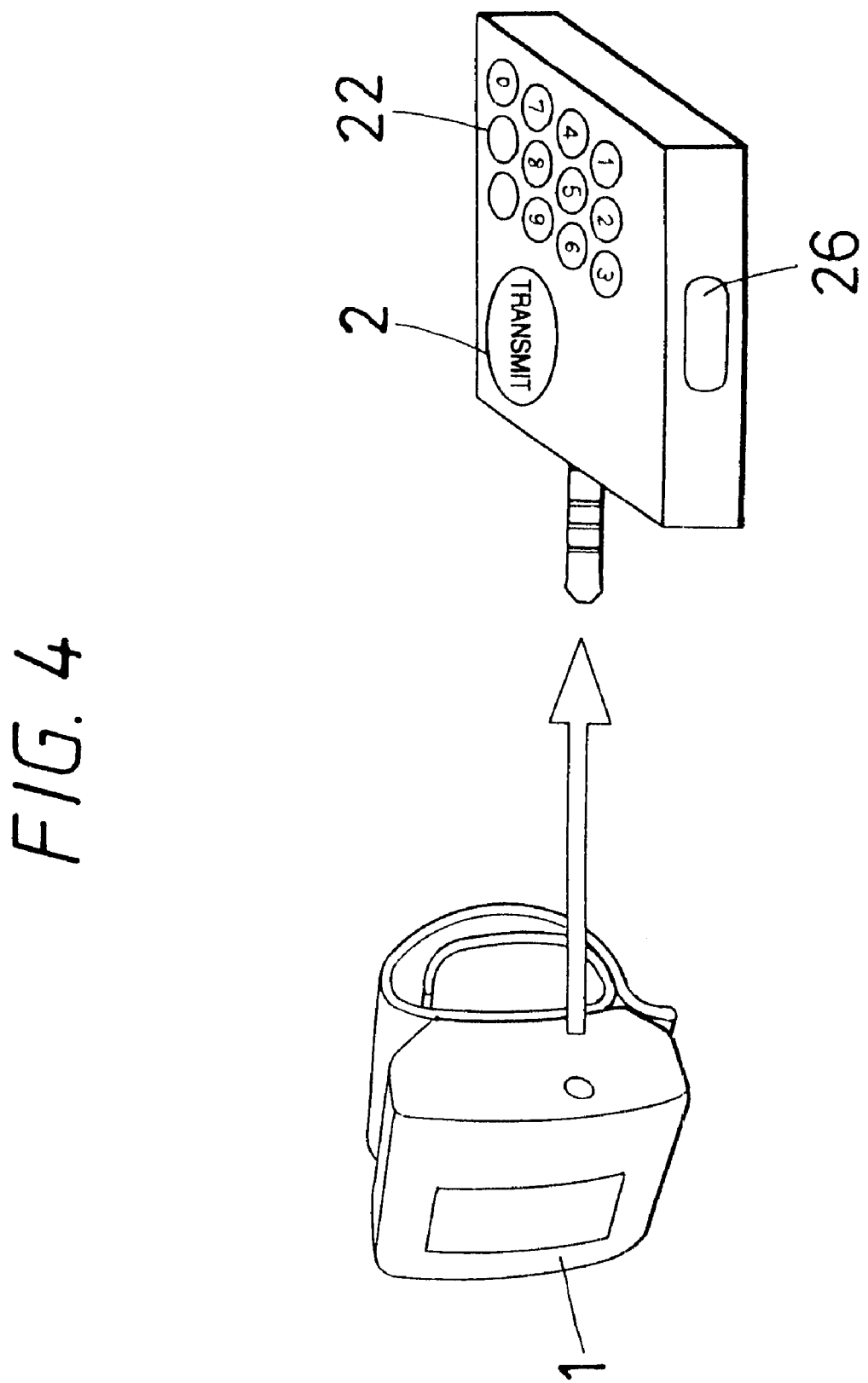
FIG. 4 is a schematic view showing an example of the connection between the health measuring device and the data transferring device.
Figure 5:
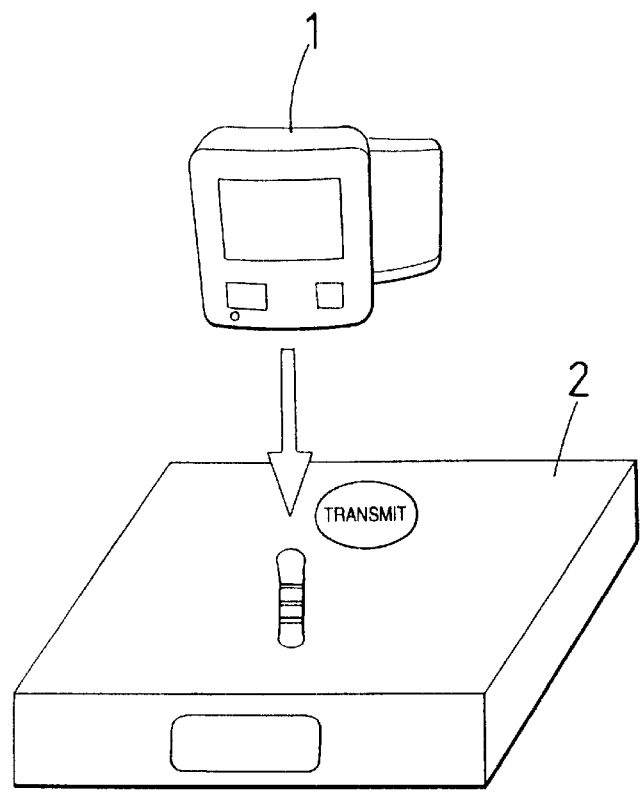
FIG. 5 is a schematic view showing the data transferring device.
Figure 6:
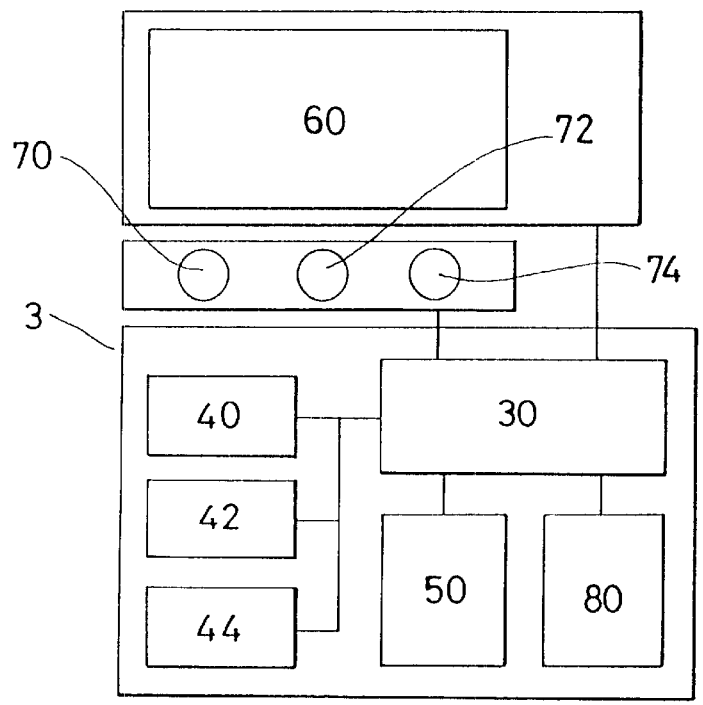
FIG. 6 is a block diagram showing the internal structure of the terminal device.

A first embodiment of the present invention will now be described with reference to FIGS. 1 to 6. FIG. 1 is a block diagram showing an in-home health caring system according to the present invention. FIG. 2 is a block diagram showing the internal structure of a health measuring device. FIG. 3 is a block diagram showing the internal structure of the data transferring device. FIG. 4 is a schematic view showing an example of the connection between the health measuring device and the data transferring device. FIG. 5 is a schematic view showing the data transferring device. FIG. 6 is a block diagram showing the internal structure of the terminal device.

As shown in FIG. 1 the in-home health caring system according to the present invention incorporates a home-side system having health measuring devices 1a to 1n, a data transferring device 2 and a terminal device 3. Moreover, the in-home health caring system incorporates a center device 5 disposed in an external hospital, medical examination center, a caring center or the like connected to the terminal device 3 of the home-side system through a communication infrastructure 4.

The health measuring devices 1a to in may be a sphygmomanometer, a clinical thermometer, a weighing machine, a blood-sugar level meter, a pedometer and an electrocardiograph. If the health measuring device is able to measure the state of the health in a home, the device is not limited. One device may be employed or a plurality of devices may be combined with one another to be adaptable to a state of a user.

As shown in FIG. 2, the health measuring devices 1a to 1n incorporate means 10a to 10n for measuring data about the health, means 12a to 12n for storing measured data, transmitting means 14a to 14n for inputting stored data to the data transferring device 2 and control means 16a to 16n for controlling the foregoing means.

The means 10a to 10n for measuring data about the health are means for measuring the blood pressure when the means are sphygmomanometers. When the means are clinical thermometers, the means are means for measuring the body temperature. The means 10a to 10n are different among the health measuring devices 1a to 1n. Also the means 12a to 12n for storing measured data are different among the health measuring devices 1a to 1n. Note that the transmitting means 14a to 14n for inputting stored data to the data transferring device 2 are means for satisfying a common standard for all of the health measuring devices 1a to 1n. As a result, data can be read by one data transferring device 2 which is shared by all of the health measuring devices 1a to 1n.

The data transferring device 2, as shown in FIG. 3, incorporates, a means 20 for reading data transmitted by the health measuring devices 1a to 1n, a means 22 for inputting numerals, characters and graphics, a storage means 24 for storing read data and supplied data about numerals, characters and graphics, a means 26 for transmitting stored data to the terminal device and a control means 28 for controlling the foregoing means.

The terminal device 3, as shown in FIG. 6, incorporates a microprocessor 30 for controlling the terminal device 3; a ROM 40 in which an OS and application software have been stored; a RAM 42 serving as a work area; a flash memory 44 for holding data; a means 50 for receiving data wireless-transmitted from the data transferring device 2; an LCD monitor 60; operation buttons 70, 72 and 74; and a communication means 80 for performing data communication with outside.

The center device 5 is constituted by a usual personal computer and an interface device for the communication network, the center device 5 being capable of periodically and automatically collecting data about the health stored in the terminal device 3 through the communication infrastructure 4.

As shown in FIG. 4, data communication between the health measuring devices 1a to 1n and the data transferring device 2 is performed by establishing electrical connection of communication terminals. The communication is performed through female terminals provided for the health measuring devices 1a to 1n (which are electronic sphygmomanometers serving as health measuring devices in FIG. 4). Moreover, male terminals provided for the data transferring device 2 are used. Simultaneously with the connection of the health measuring devices 1a to 1n, data transmitted from the health measuring devices 1a to 1n is received so as to be wireless-transmitted to the terminal device 3. If there is a requirement from a state in which the data transferring device 2 is operated, data storage means and a transmission button may furthermore be provided. Thus, data received from the health measuring devices 1a to 1n is temporarily stored, followed by wireless-transmitting data to the terminal device 3 after the transmission button has been depressed. The data transferring device 2 may be formed into a portable structure as shown in FIG. 4. As an alternative to this, a stationary structure which permits the health measuring device to be disposed as shown in FIG. 5 may be employed.

When data communication between the health measuring devices 1a to 1n and the data transferring device 2 is performed by establishing the electrical connection of their communication terminals as described above, required circuits can be realized with considerably low cost as compared with the circuits for use in the wireless communication using infrared rays or electric waves.

When all of the health measuring devices 1a to 1n are provided with the wireless communication function and a multiplicity of types of the health measuring devices 1a to 1n are employed, the cost of the in-home health caring system is enlarged. On the other hand, the in-home health caring system according to this embodiment has the structure that one data transferring device 2 is provided which can be shared by all of the health measuring devices 1a to 1n. Therefore, enlargement of the cost can be prevented to provide the in-home health caring system which is able to realize wireless input of data to the terminal device 3 and which can easily be operated.

The data transferring device 2 may be provided with a means for identifying each user. The means for identifying each user may be any one of a button having name of the user written thereon, a device for reading the fingerprint and the like. The identifying means must be capable of identifying a user.

Usually, there is a possibility that the in-home health caring system is used by a plurality of persons in a home. The terminal device 3 must recognize the person, the health data of which has been received. As a recognizing means, a method may be employed with which names having the possibility of using the system are previously registered in the terminal device 3. When the terminal device 3 has received data from the data transferring device 2, the names of the registered persons are displayed on the LCD monitor 60 to cause a person which must be cared to be selected by operating the operation buttons 70, 72 and 74. However, if the foregoing method is employed, the user must move to the terminal device 3, that is, the system cannot conveniently be used.

On the other hand, the in-home health caring system according to this embodiment incorporates the data transferring device 2 which is capable of identifying a user. Therefore, when health data is transmitted from the data transferring device 2 to the terminal device 3, ID data of the identified user is transmitted together with health data. Thus, the terminal device 3 is able to recognize the person, the health data of which has been received. As a result, input of health data to the terminal device 3 from a remote position is permitted if the in-home health caring system is used by a plurality of persons. Therefore, the system can considerably easily be operated.

The data transferring device 2 may be enabled to remote-control the terminal device 3. As a means for remote-controlling the terminal device 3 by the data transferring device 2, buttons equivalent to the operation buttons 70, 72 and 74 may be provided for the upper surface of the data transferring device 2. Moreover, the means 22 for performing the wireless transmission is used to transmit a control code corresponding to the operation of the button. In accordance with the received control code, the terminal device 3 is operated similarly to the case where the operation of any one of buttons 70, 72 and 74 has been performed.

The terminal device 3 is able to display a graph of stored health data and perform data communication to the outside through the communication infrastructure 4. To perform the foregoing operations, the operation buttons 70, 72 and 74 provided for the upper surface of the terminal device 3 must be operated in a usual case. In the foregoing case, the user must move to the terminal device 3. Therefore, the system cannot conveniently be used.

The in-home health caring system according to this embodiment enables the data transferring device 2 to remote-control the terminal device 3. Therefore, all of the operations of the terminal device 3 can be performed from a remote position. As a result, the system can significantly easily be operated.

In the foregoing in-home health caring system, if data about the health is measured by a device (for example, a weighing machine or the like which has been provided for the home) which has not been considered to be the health measuring device for the system, data cannot be input to the data transferring device. Therefore, data of health measuring devices 1'a to 1'n having no function for transferring measured data is first visually confirmed by a user. A result of the confirmation may be input to the data transferring device 2 through a means 22 for inputting numerals, characters and graphics. A ten-key corresponds to the means 22 which inputs numerals, characters and graphics which is provided for the data transferring device. The means 22 may be a pressure-sensitive pad, a touch panel or the like as well as the ten-key. Any means which is capable of inputting numerals, characters and graphics may be employed.

The in-home health caring system according to this embodiment enables data measured by health measuring devices 1'a to 1'n, which has not been considered to be employed in the conventional in-home health caring system, to be input to the data transferring device 2.

An input device 6 incorporating means for inputting numerals, characters and graphics and means for wireless-transmitting input data to the terminal device 3 may be provided. Data measured by the health measuring devices 1'a to 1'n having no transferring function is input by a method with which data measured by the health measuring devices 1'a to 1'n is confirmed by a user in a visual manner or the like similarly to the foregoing system. A result of the confirmation is input to the input device 6, and then the result is wireless-transmitted to the terminal device 3.

The in-home health caring system according to the present invention incorporates the input device 6 with which data measured by the health measuring devices 1'a to 1'n having no transferring function can be input to the terminal device 3. Therefore, an in-home health caring system which can easily be operated can be provided. Since the input device 6 is individually provided for the data transferring device 2, the position of each device may arbitrarily be determined.

Second Embodiment

A second embodiment of the present invention will now be described with reference to FIGS. 7 to 34.

Figure 7:
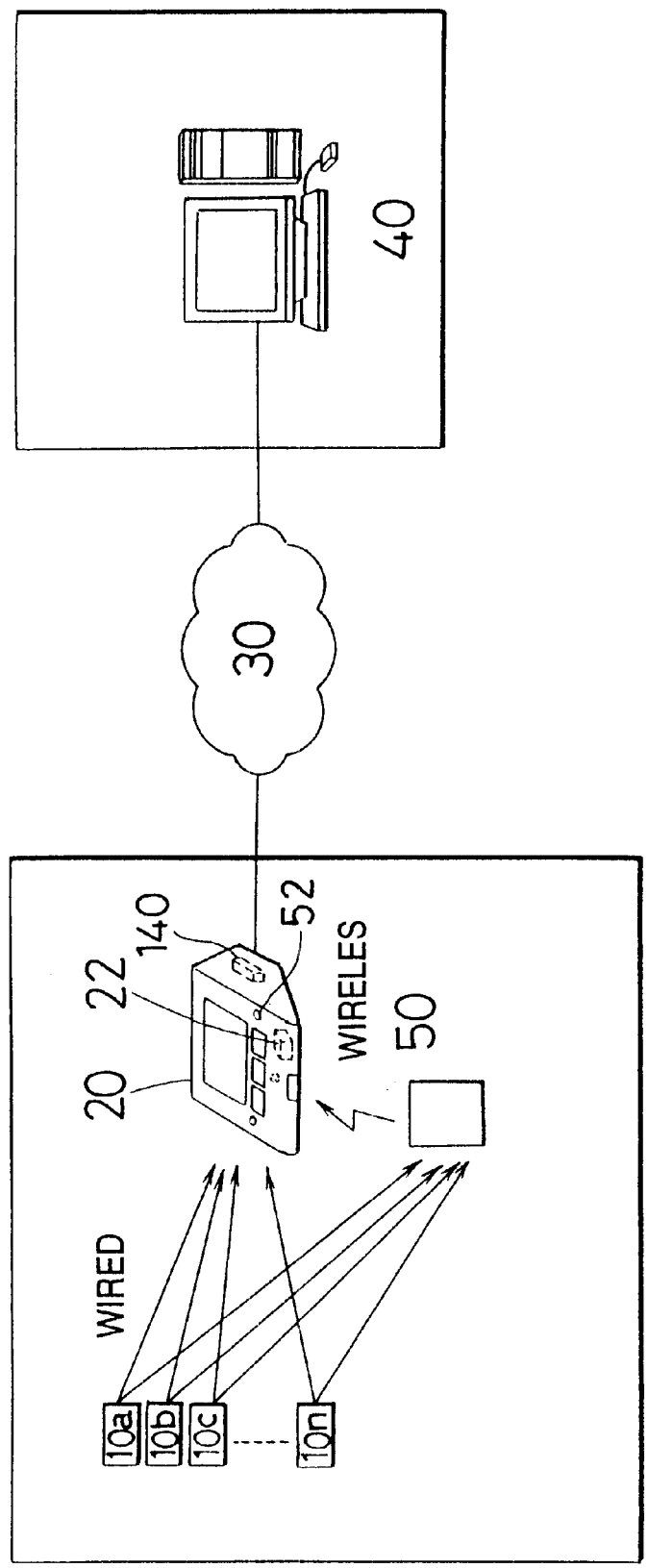
FIG. 7 is a schematic view showing the structure of an in-home health caring system according to the present invention.
Figure 9:
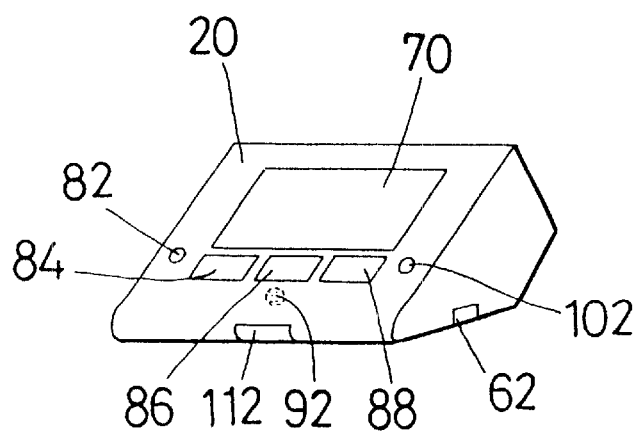
FIG. 9 is a schematic perspective view showing a terminal device.
Figure 10:
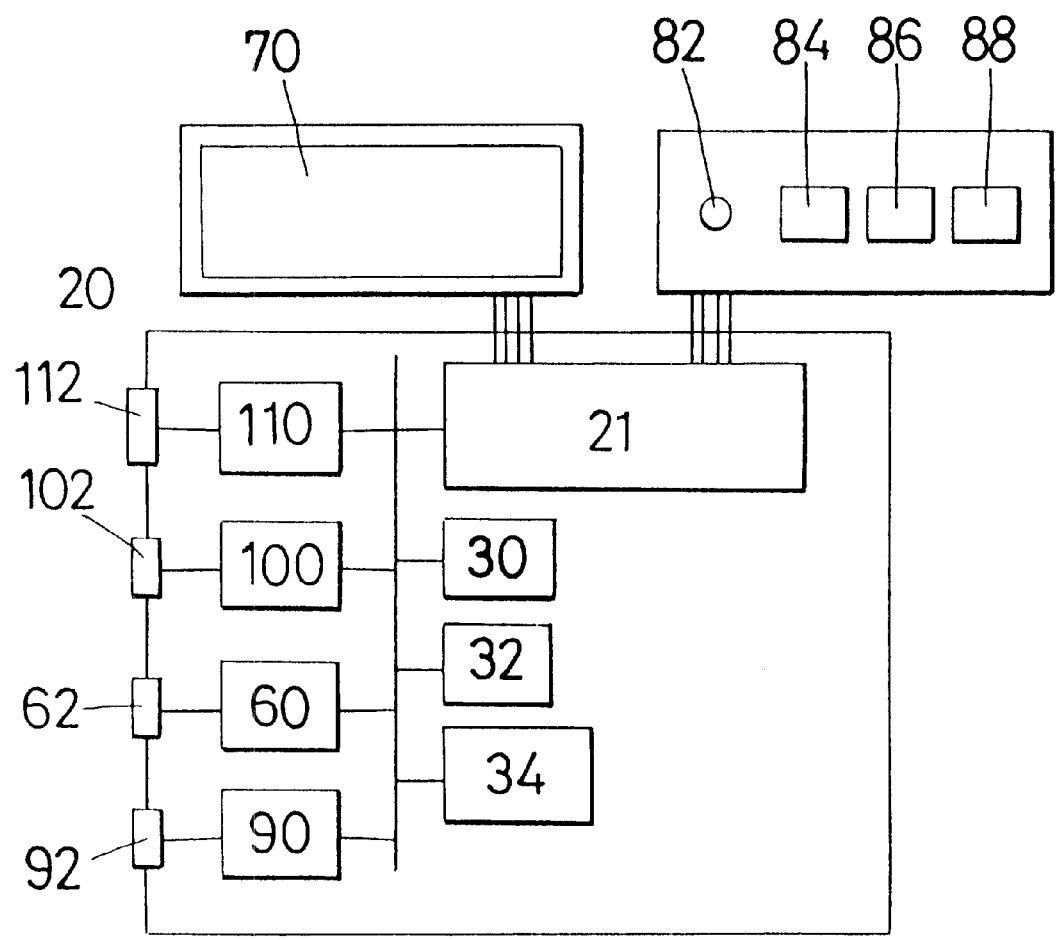
FIG. 10 is a block diagram showing the internal structure of a terminal device.
Figure 11:
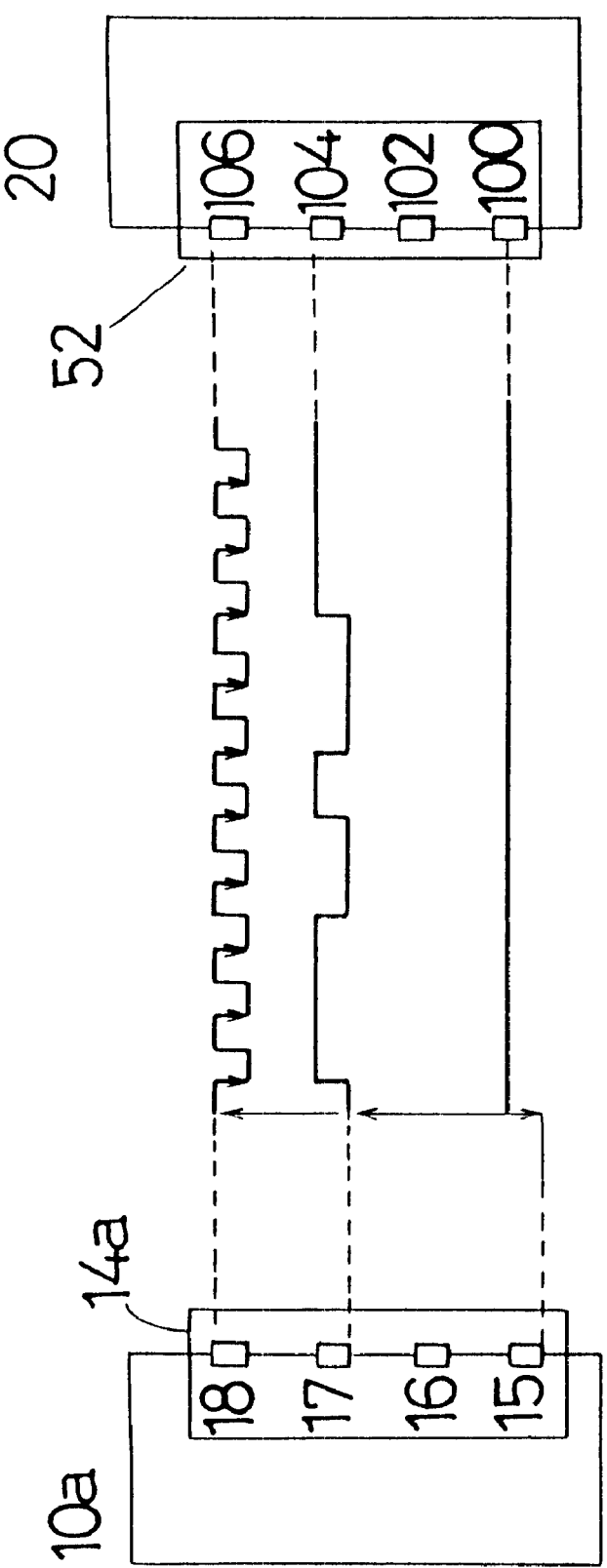
FIG. 11 is a diagram showing a communication method of synchronous serial communication.
Figure 12:
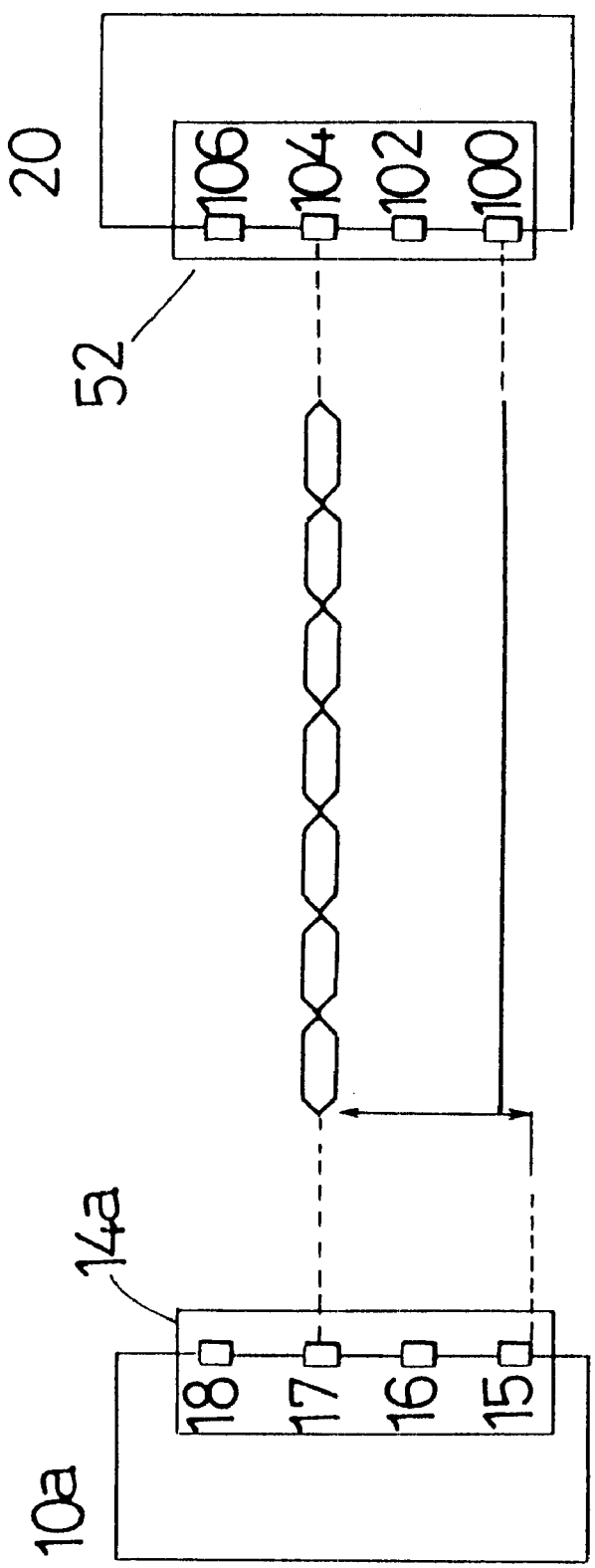
FIG. 12 is a diagram showing a communication method of start-stop serial communication.
Figure 13:
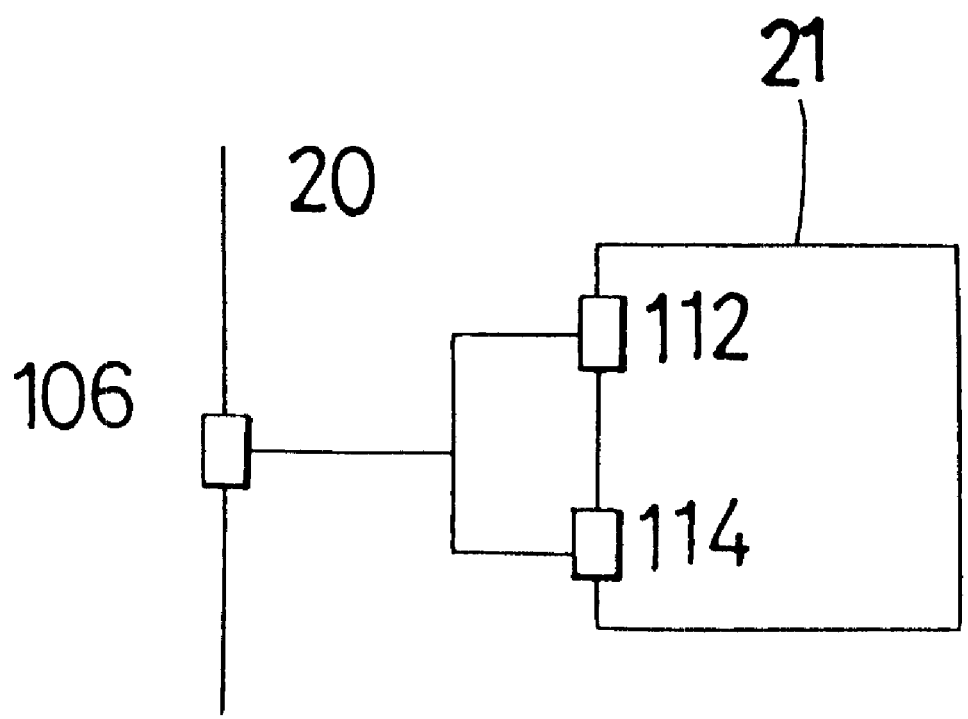
FIG. 13 is a block diagram showing a signal branched portion of the terminal device.
Figure 14:
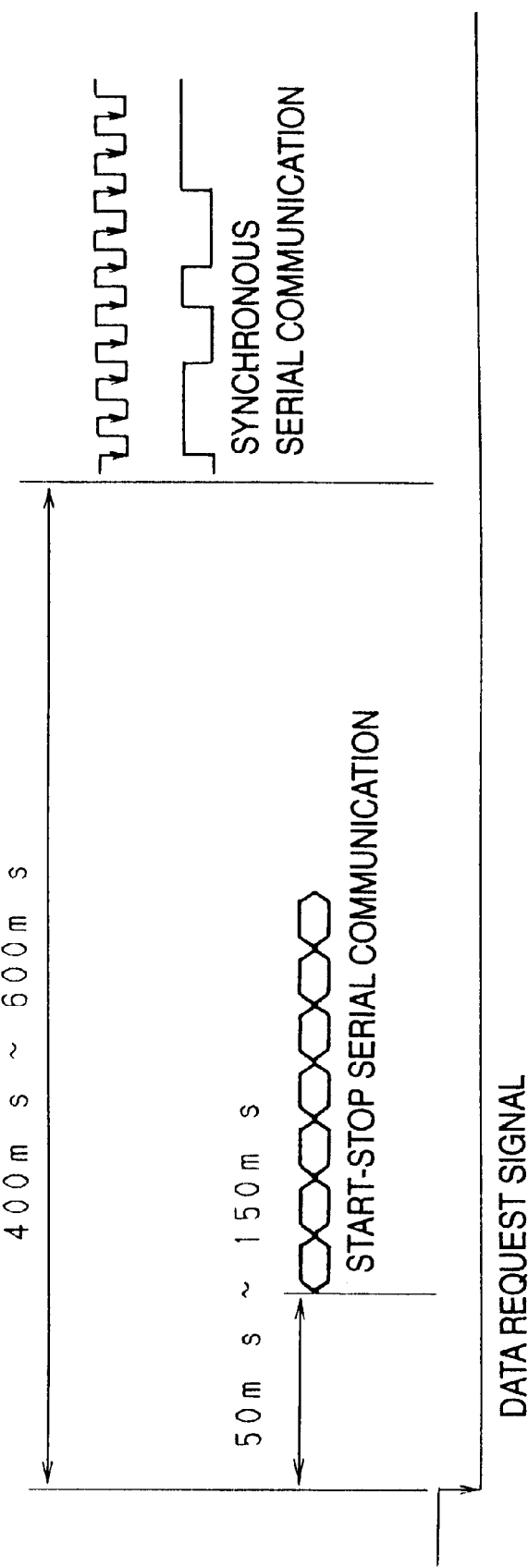
FIG. 14 is a timing chart for each signal method.
Figure 15:
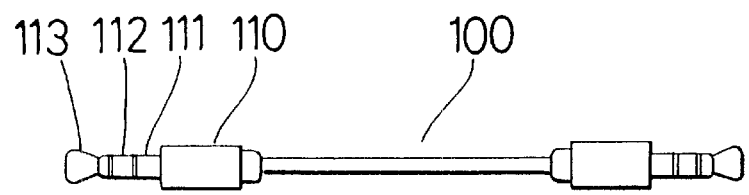
FIG. 15 is a schematic view showing a communication cable.
Figure 16:
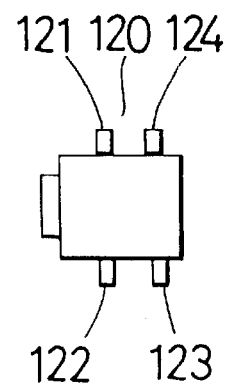
FIG. 16 is a schematic view showing a plug.
Figure 17:
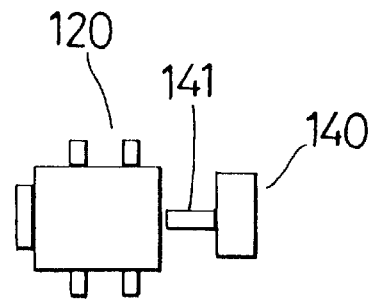
FIG. 17 is a schematic view showing a detecting means.
Figure 18:
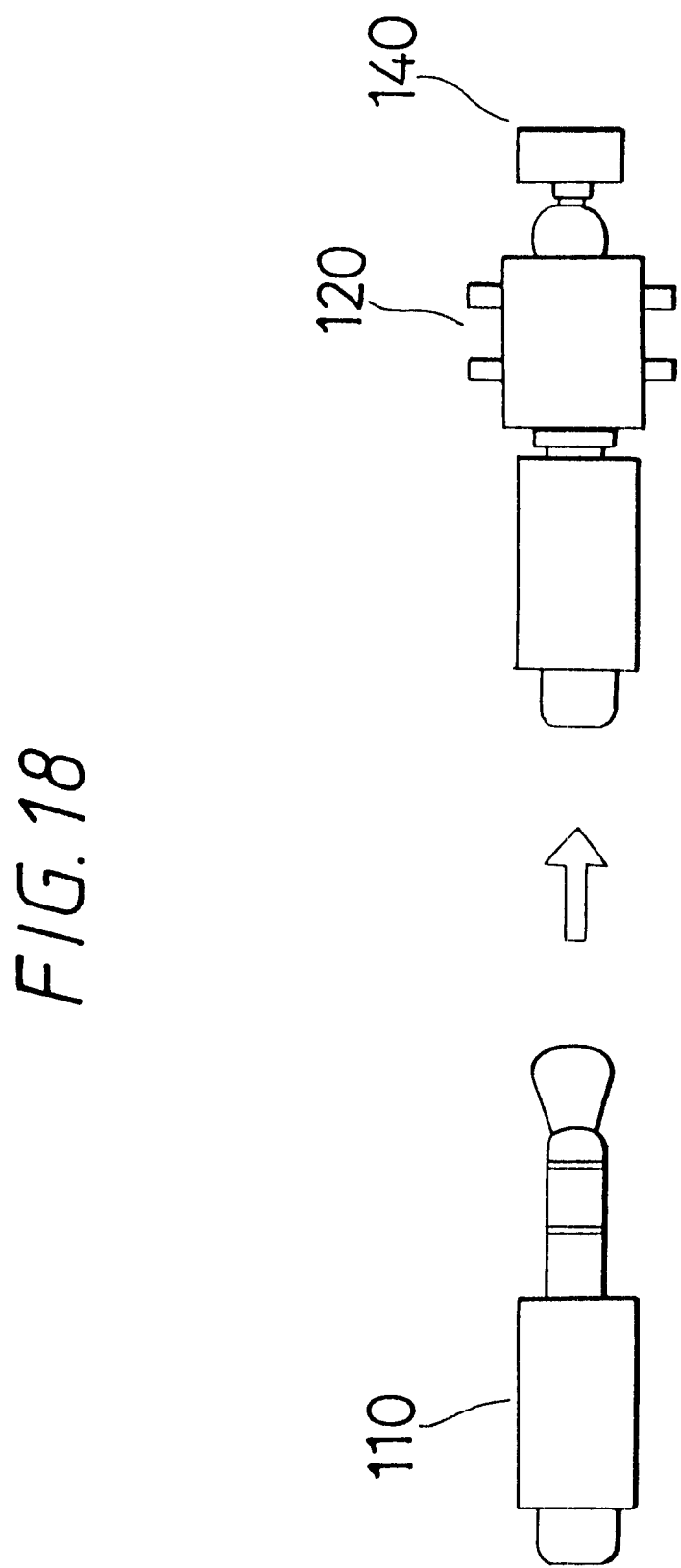
FIG. 18 is a schematic view showing another detecting means.
Figure 19:
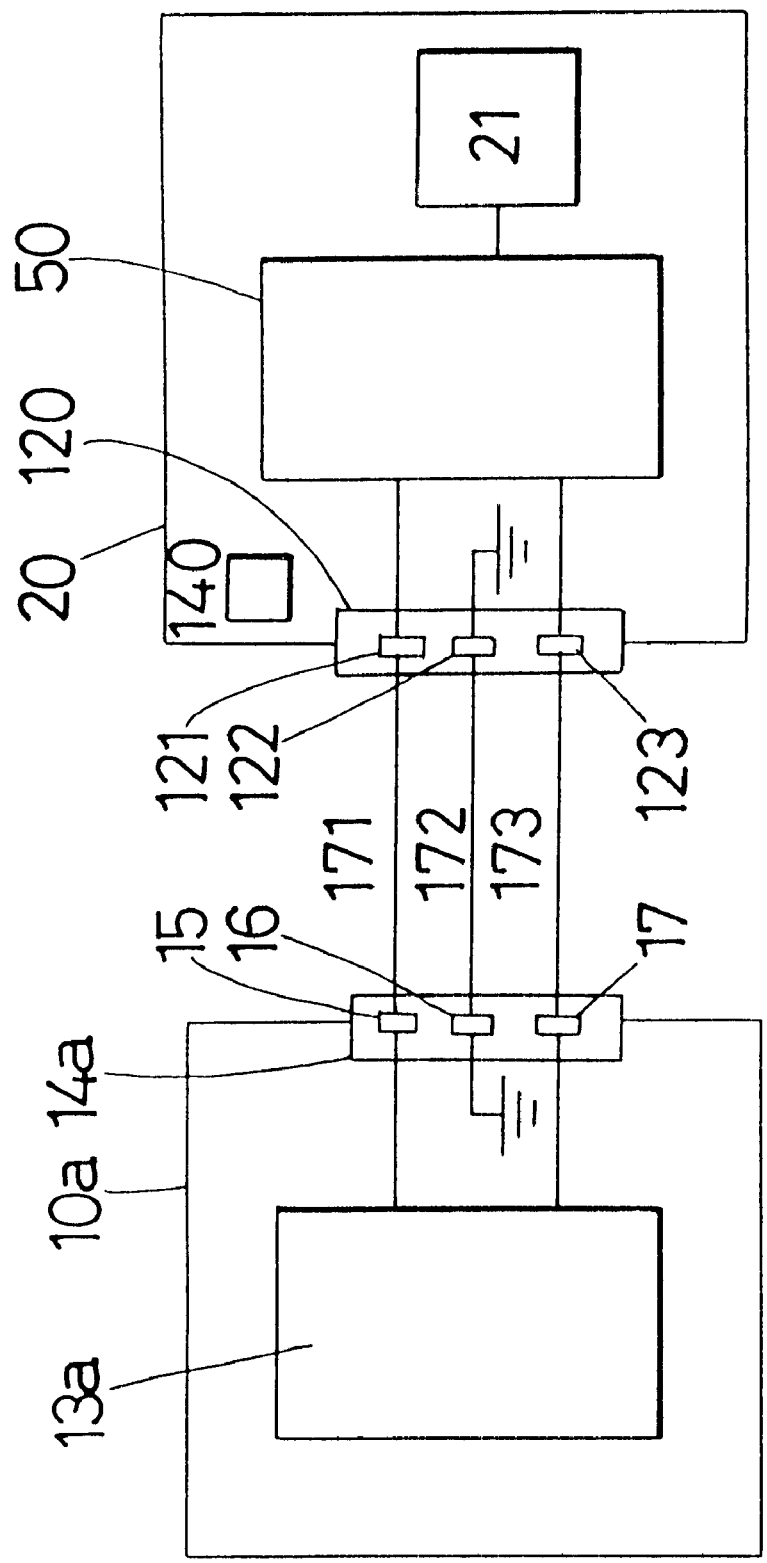
FIG. 19 is a block diagram showing a state of the connection between the health measuring unit and the terminal unit.
Figure 20:
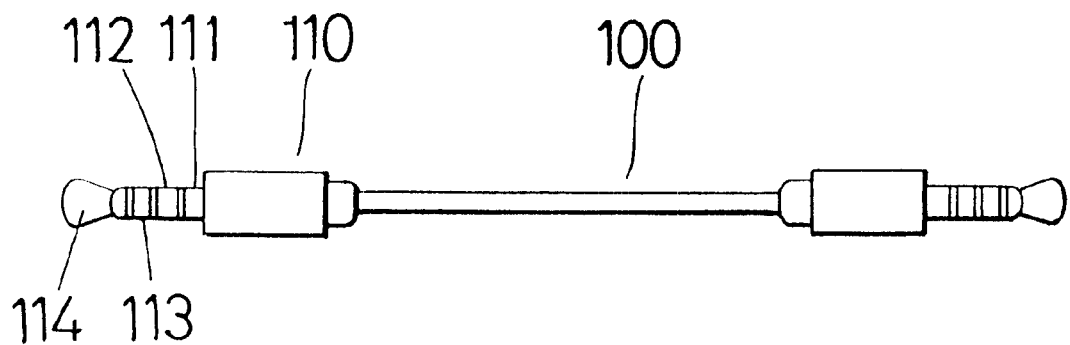
FIG. 20 is a schematic view showing another communication cable.
Figure 21:
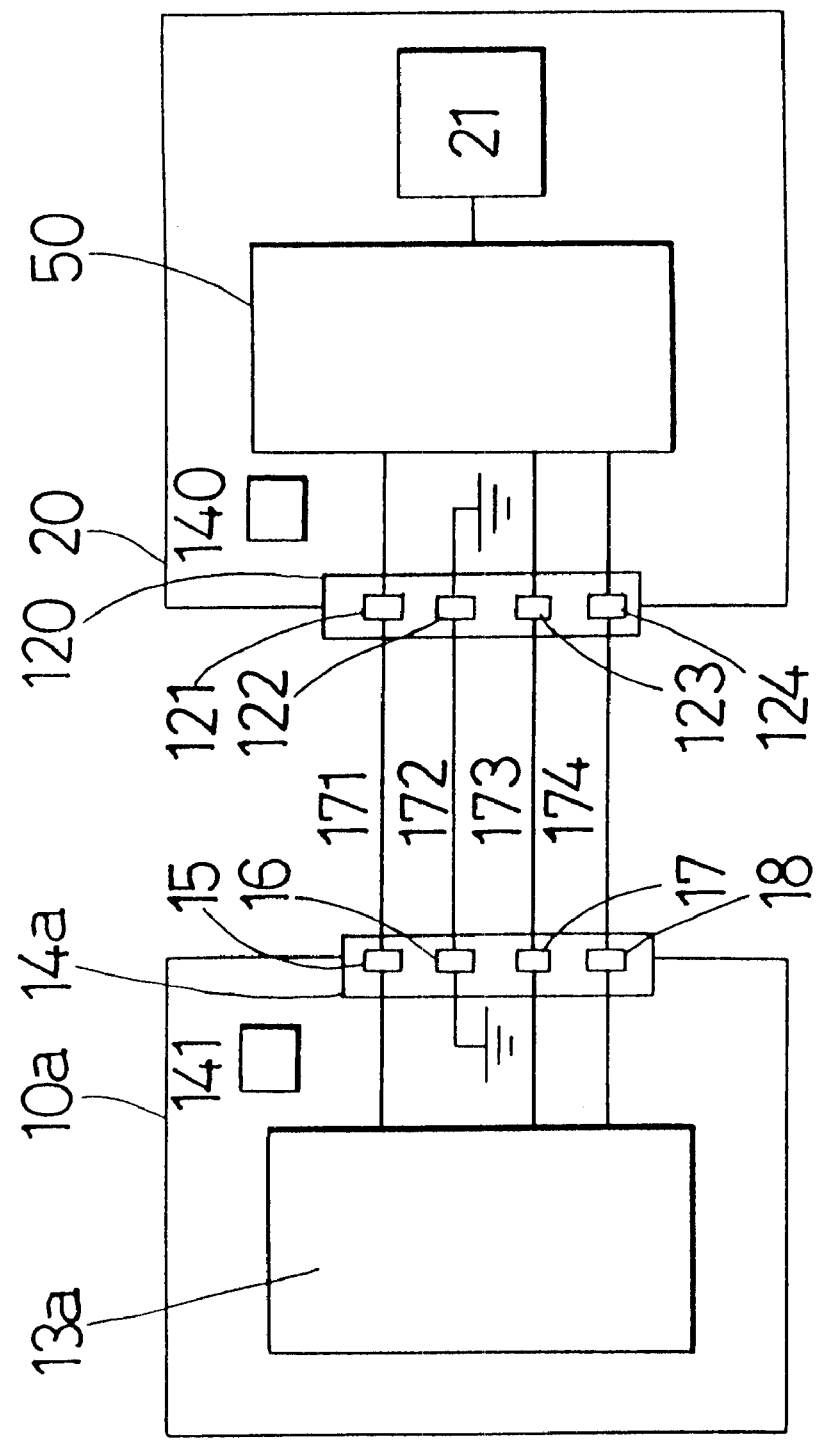
FIG. 21 is a block diagram showing a state of the connection between another health measuring unit and the terminal unit.
Figure 22:
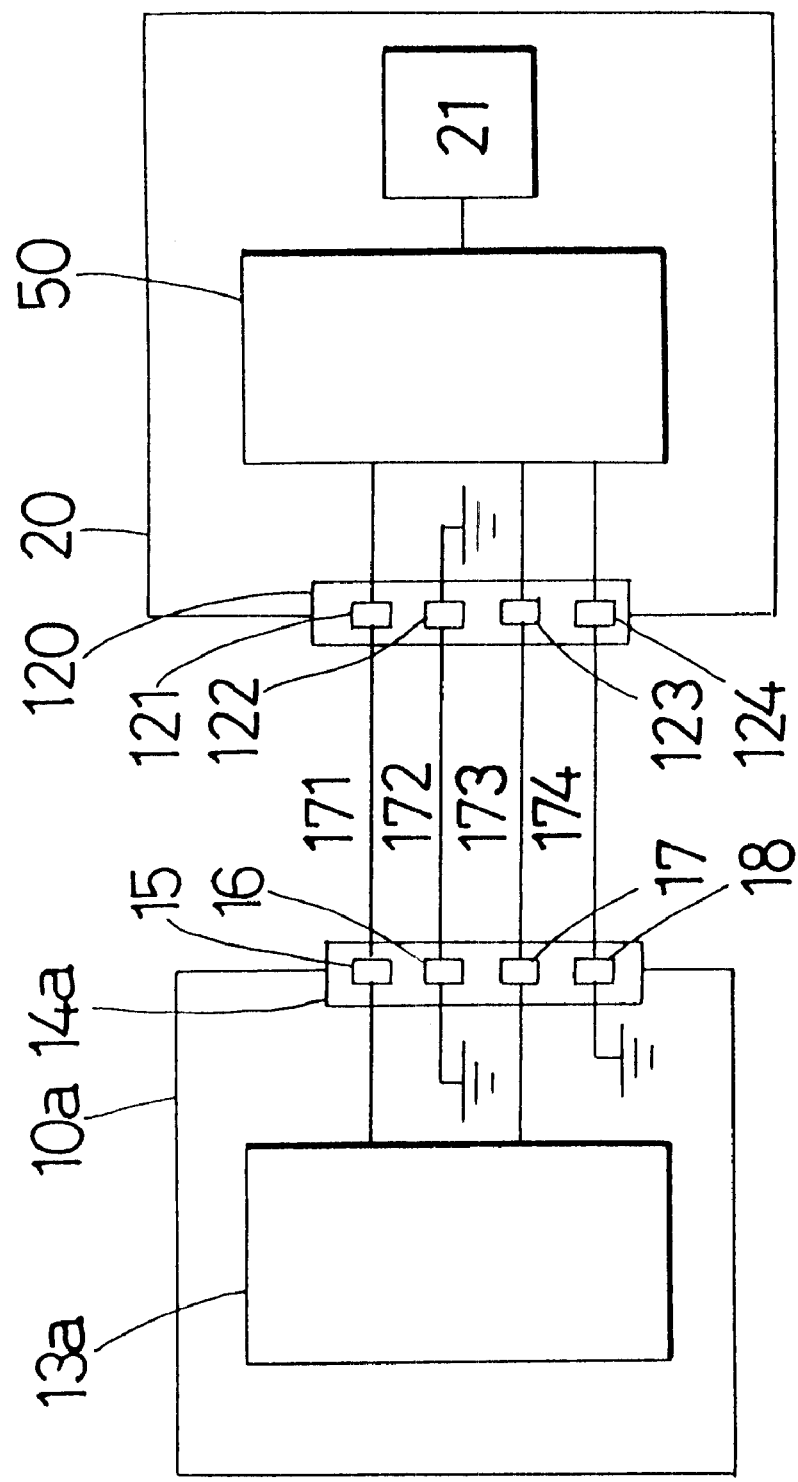
FIG. 22 is a block diagram showing a state of the connection between another health measuring unit and the terminal unit.
Figure 23A:
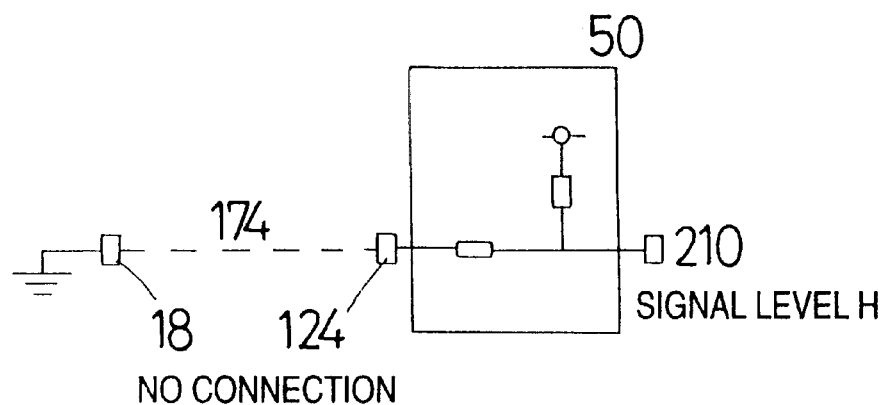
Figure 23B:
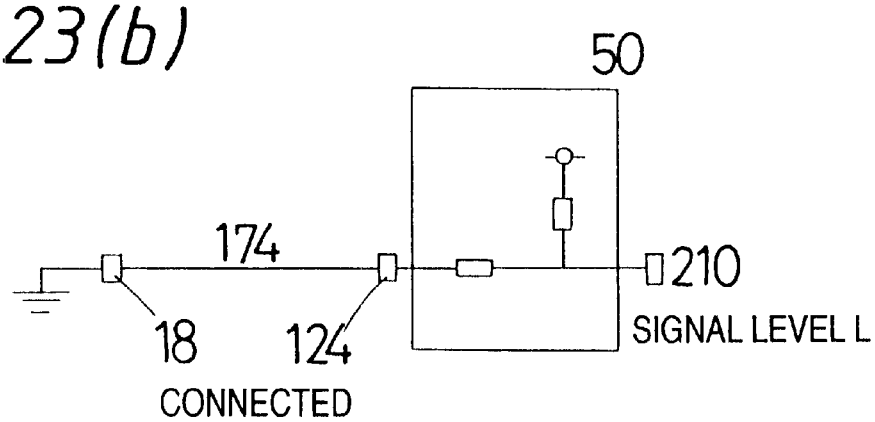
Figure 24:
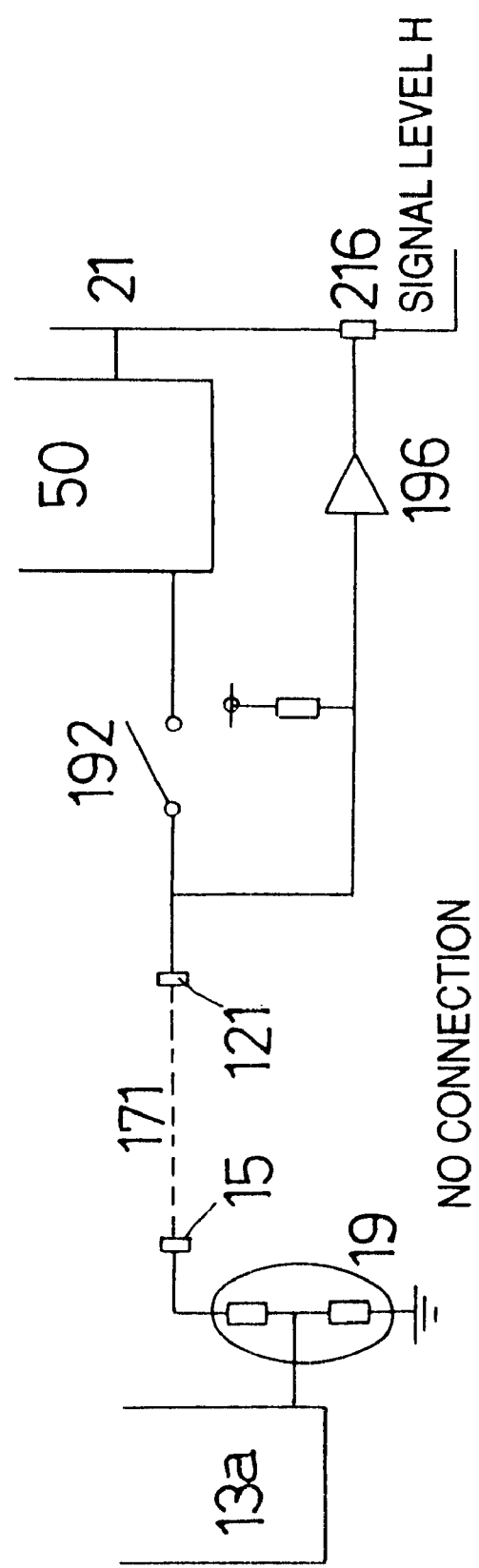
FIG. 24 is a block diagram showing another detecting means in a non-connection state.
Figure 25:
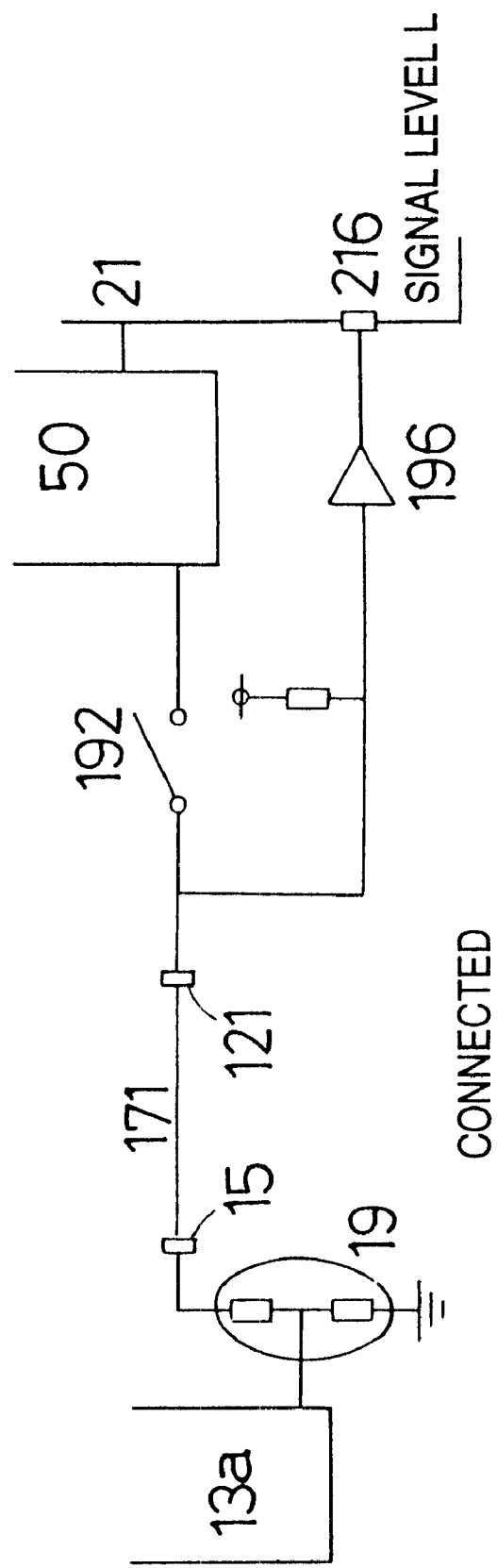
FIG. 25 is a block diagram showing another detecting means in a connected state.
Figure 26:
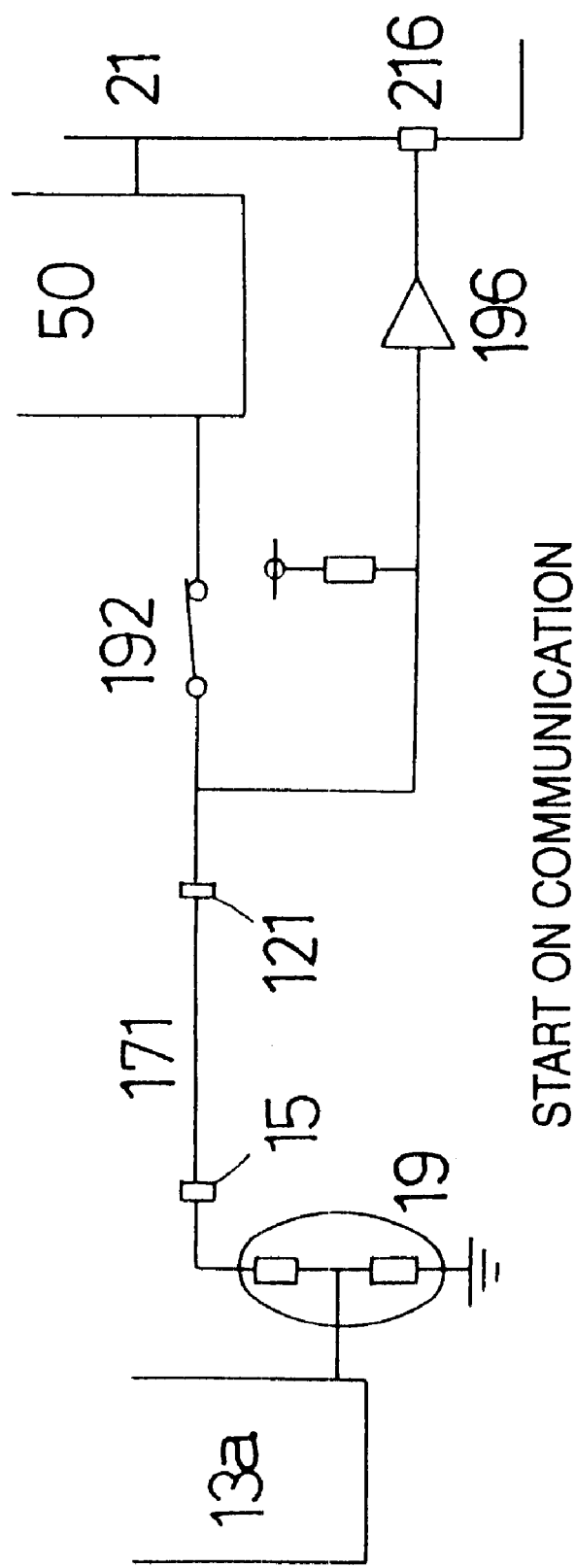
FIG. 26 is a block diagram showing another detecting means in a state where communication has been started.
Figure 27:
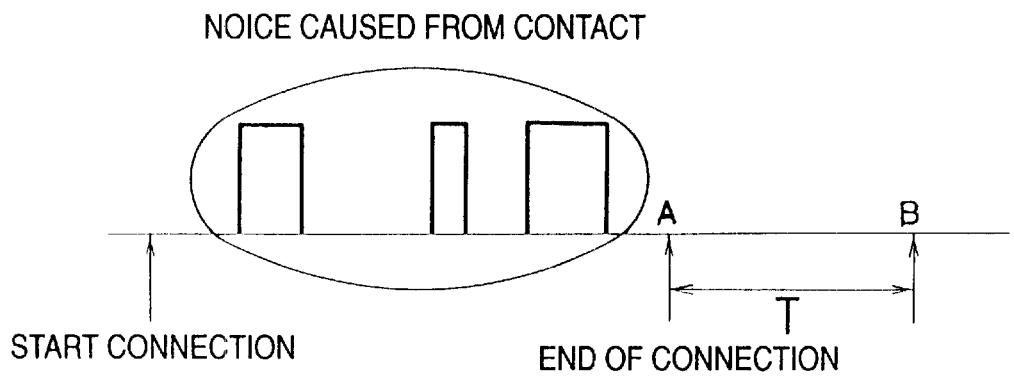
FIG. 27 is a timing chart of a signal from establishment of the connection of the health measuring unit with the terminal unit and completion of the connection.
Figure 28:
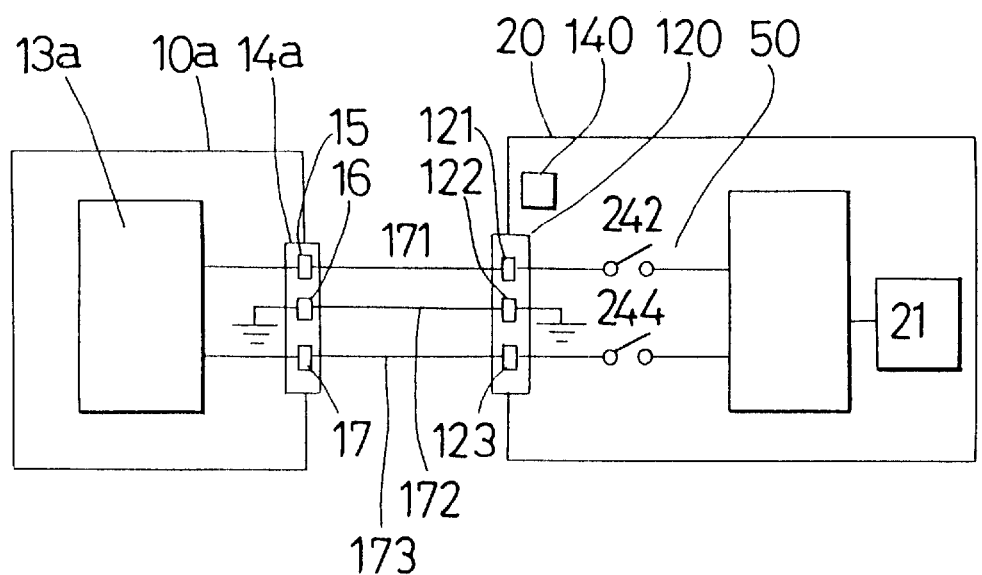
FIG. 28 is a block diagram showing a state of the connection between another health measuring unit and the terminal unit.
Figure 29:
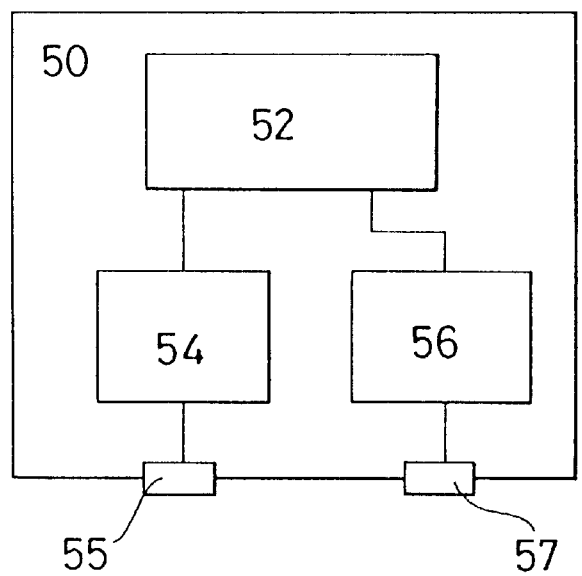
FIG. 29 is a block diagram showing a data transferring unit.
Figure 30:
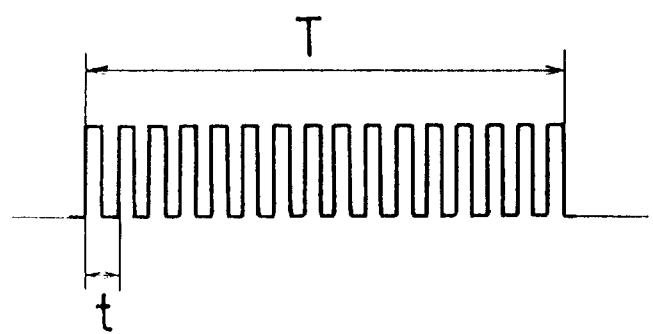
FIG. 30 is a graph showing the waveform of a basic signal for infrared-ray communication.
Figure 31:
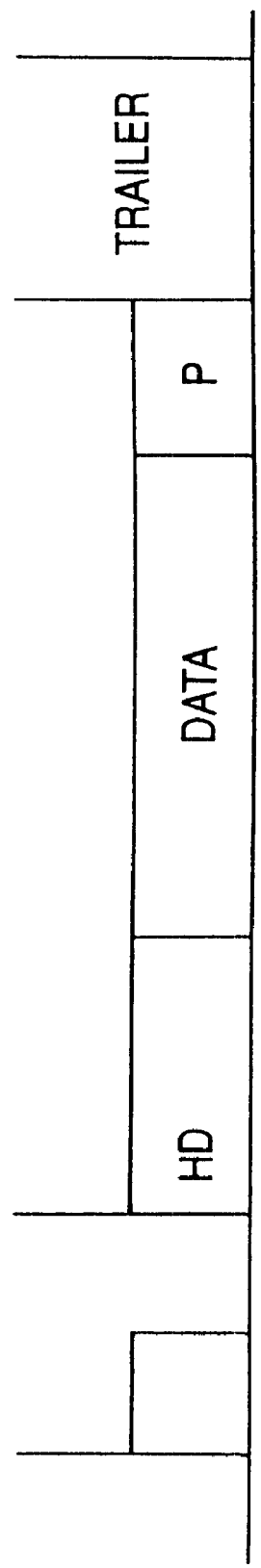
FIG. 31 is a diagram showing data format for an infrared-ray communication.
Figure 32:
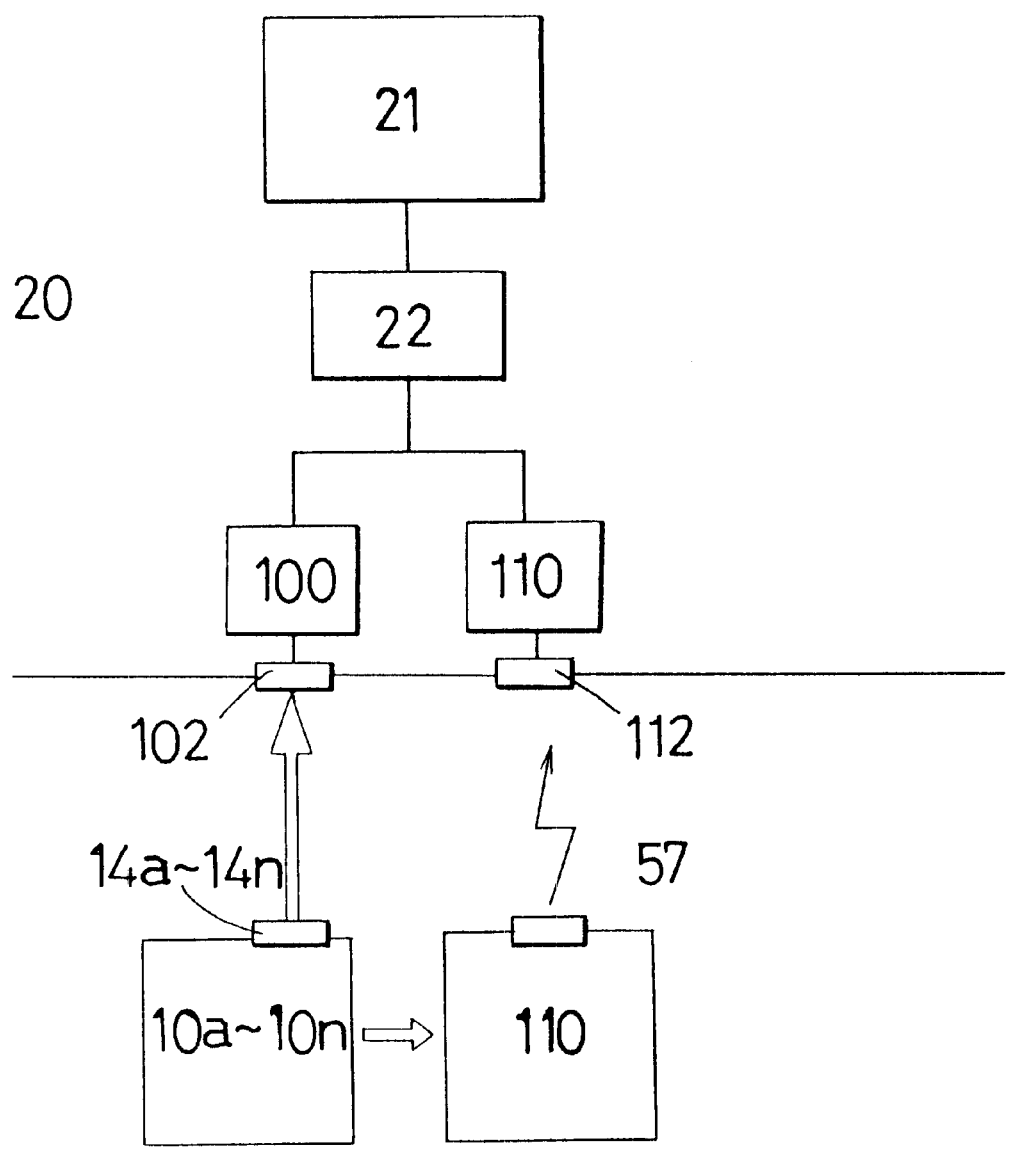
FIG. 32 is a block diagram showing an essential portion for controlling communication of data.
Figure 33:
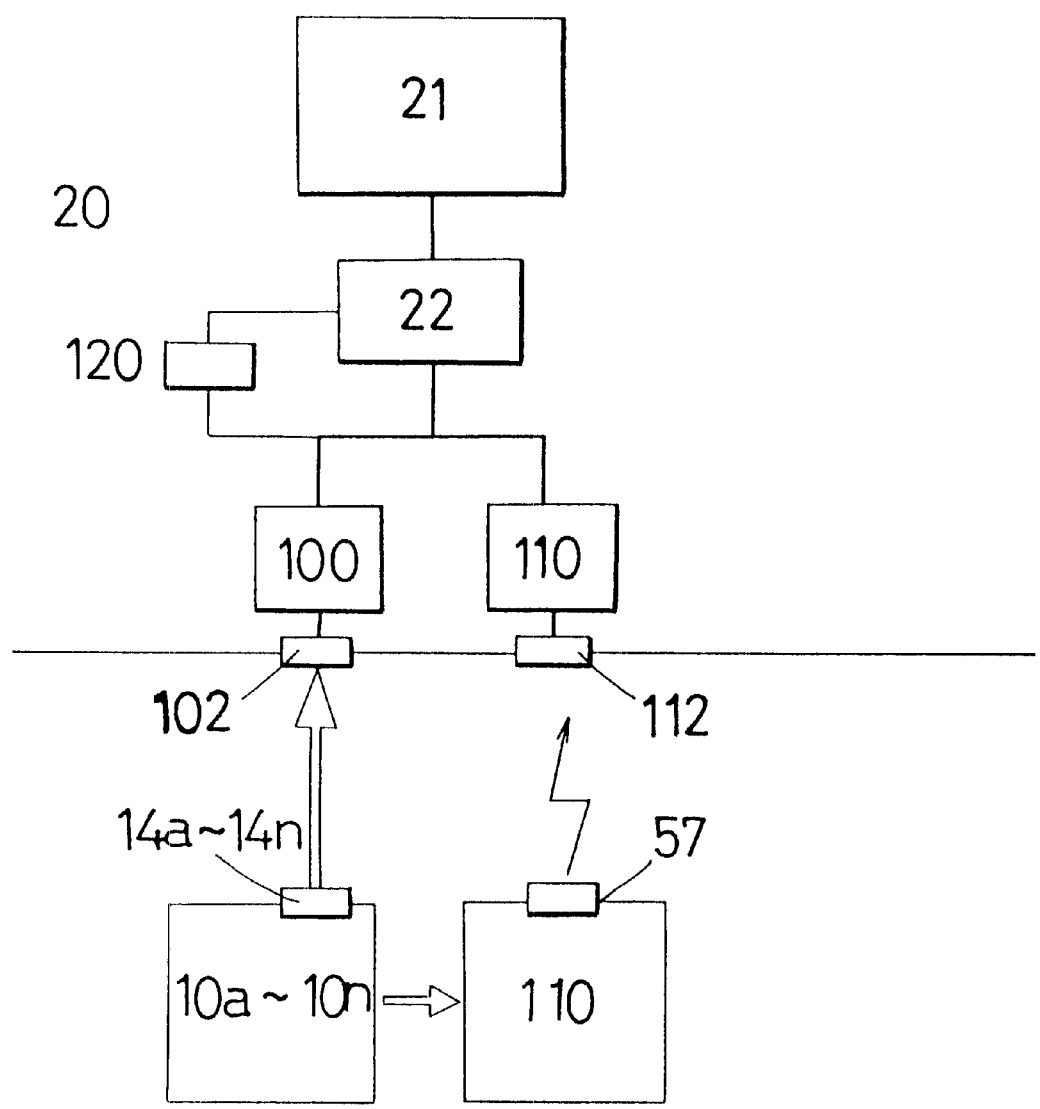
FIG. 33 is a block diagram showing an essential portion for controlling another communication of data.
Figure 34:
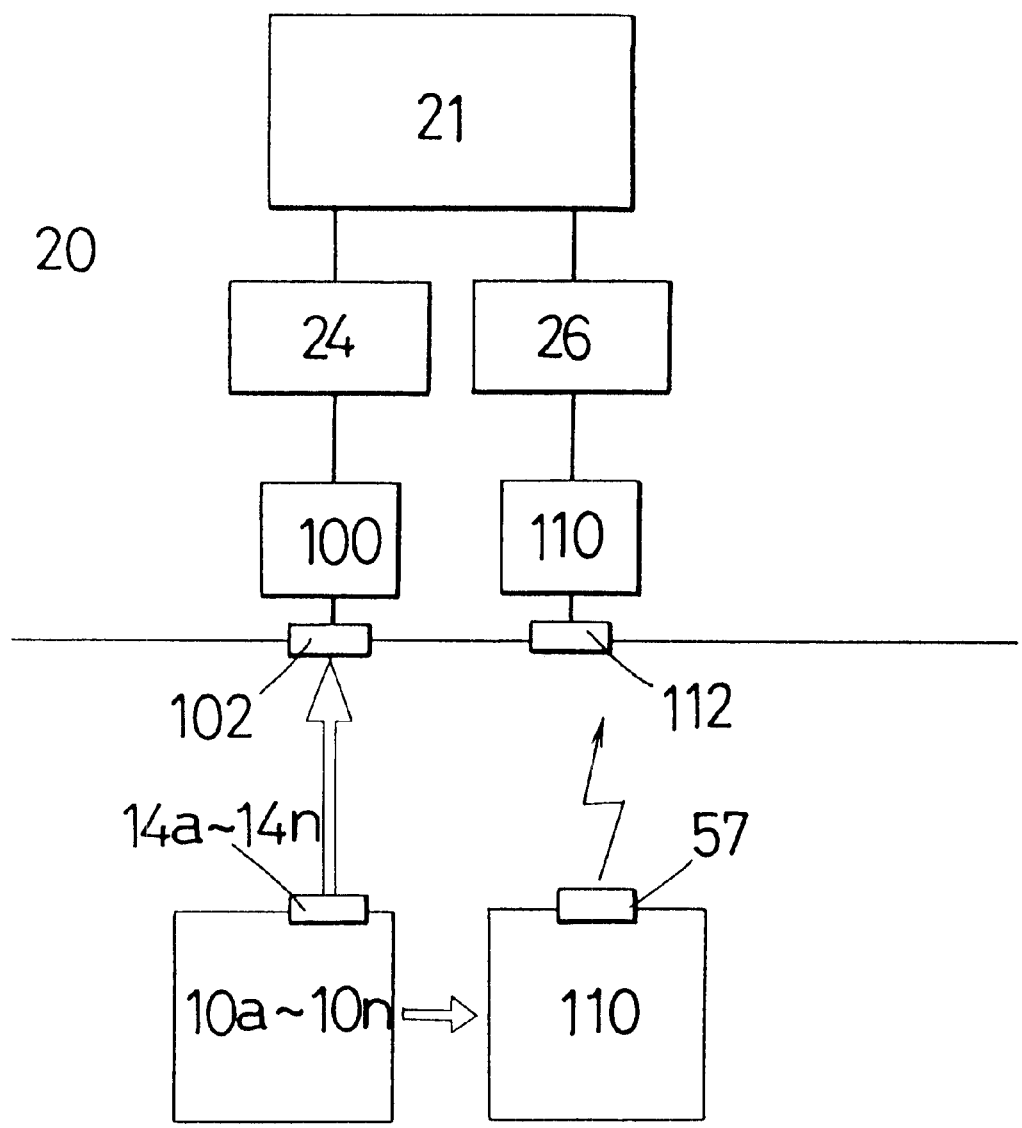
FIG. 34 is a block diagram showing an essential portion for controlling another communication of data.
Figure 35:
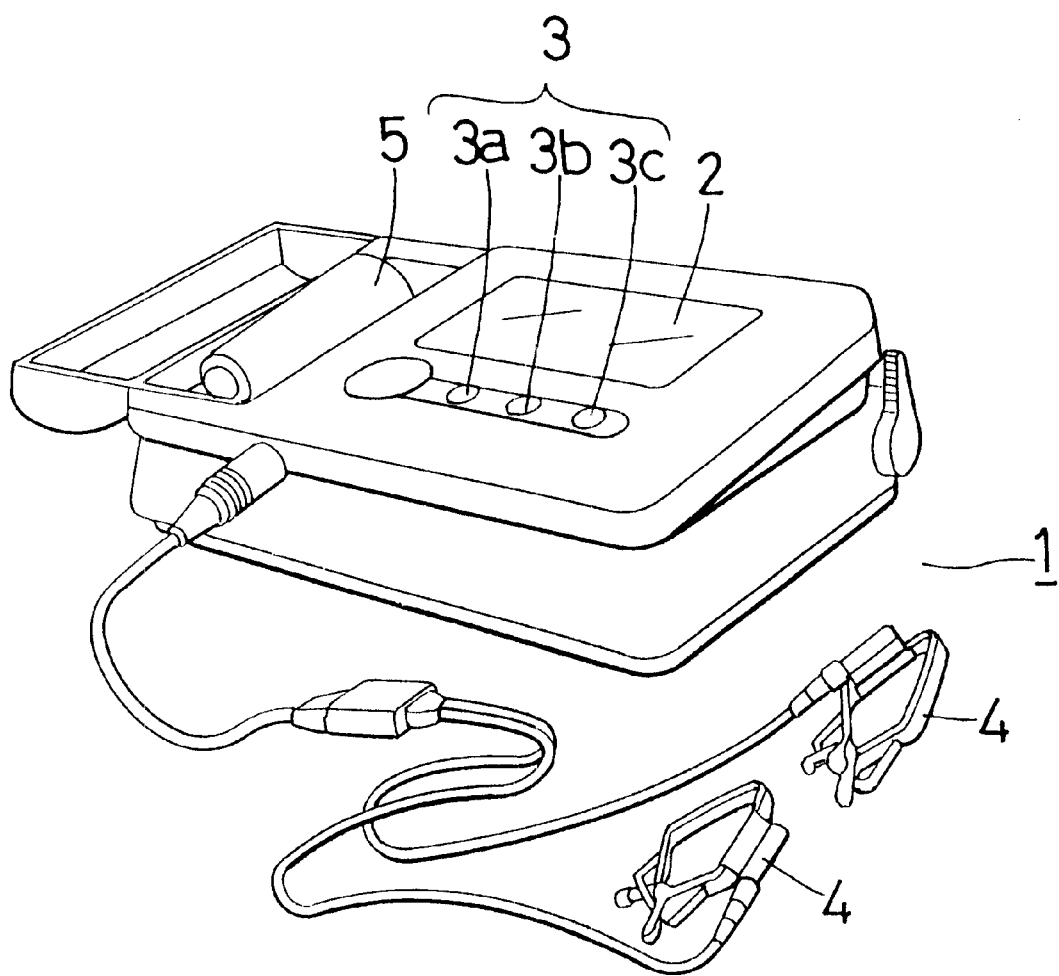
FIG. 35 is a schematic view showing a conventional in-home health caring system.

FIG. 7 is a schematic view showing a second embodiment of the structure of an in-home health caring system according to the present invention. FIG. 9 is a block diagram showing the internal structure of a health measuring device. FIG. 10 is a schematic perspective view showing a terminal device. FIG. 11 is a diagram showing a communication method of synchronous serial communication. FIG. 12 is a diagram showing a communication method of start-stop serial communication. FIG. 13 is a block diagram showing a signal branched portion of the terminal device. FIG. 14 is a timing chart for each signal method. FIG. 15 is a schematic view showing a communication cable. FIG. 16 is a schematic view showing a plug. FIG. 17 is a schematic view showing a detecting means. FIG. 18 is a schematic view showing another detecting means. FIG. 19 is a block diagram showing a state of the connection between the health measuring unit and the terminal unit. FIG. 20 is a schematic view showing another communication cable. FIG. 21 is a block diagram showing a state of the connection between another health measuring unit and the terminal unit. FIG. 22 is a block diagram showing a state of the connection between another health measuring unit and the terminal unit. FIGS. 23(a) to (b) are block diagrams showing another detecting means, in which FIG. 23(a) shows a non-connection state and FIG. 23(b) shows a connection state. FIG. 24 is a block diagram showing another detecting means in a non-connection state. FIG. 25 is a block diagram showing another detecting means in a connected state. FIG. 26 is a block diagram showing another detecting means in a state where communication has been started. FIG. 27 is a timing chart of a signal from establishment of the connection of the health measuring unit with the terminal unit and completion of the connection. FIG. 28 is a block diagram showing a state of the connection between another health measuring unit and the terminal unit. FIG. 29 is a block diagram showing a data transferring unit. FIG. 30 is a graph showing the waveform of a basic signal for infrared-ray communication. FIG. 31 is a diagram showing data format for an infrared-ray communication. FIG. 32 is a block diagram showing an essential portion for controlling communication of data. FIG. 33 is a block diagram showing an essential portion for controlling another communication of data. FIG. 34 is a block diagram showing an essential portion for controlling another communication of data.

The in-home health caring system incorporates a home-side system having health measuring devices 10a to 10n and terminal device 20 for managing data about the health (hereinafter expressed as "health data") measured by the health measuring devices 10a to 10n. Moreover, the in-home health caring system incorporates a center device 40 connected to a terminal device 20 through a communication network 30 and provided for an external hospital, a medical examination center or the like.

Figure 8:
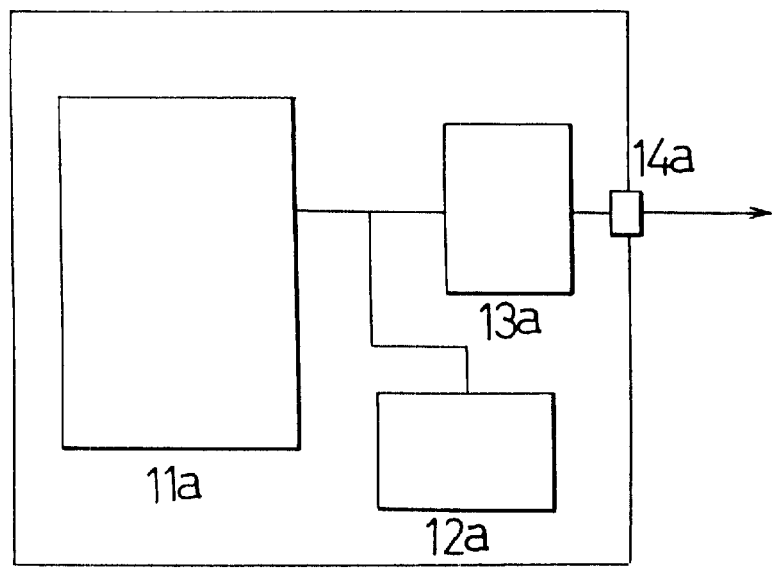
FIG. 8 is a block diagram showing the internal structure of a health measuring device.

The health measuring devices 10a to 10n, as shown in FIG. 8, incorporate measuring means 11a to 11n for measuring a state of the health, storage means 12a to 12n for storing measured health data, transmitting means 13a to 13n for transmitting stored health data to the terminal device 20 through a communication cable and terminals 14a to 14n which are connected to the communication cable 100.

The measuring means 11a to 11n are means for measuring the blood pressure if the means are the sphygmomanometers. The means are means for measuring the body temperature if the means are the clinical thermometers. Each of the health measuring devices 10a to 10n is able to measure a variety of health data items. Although the transmitting means 13a to 13n are the same means in this embodiment, the means may be individual means each using wired communication, wireless communication or infrared rays among the wireless communication. If a predetermined communication standard for the health measuring devices 10a to 10n can be satisfied, the shape of the connector and elements which must be provided are not limited. The health measuring devices 10a to 10n may be sphygmomanometers, clinical thermometers, weighing machines, body fat meters, electrocardiograph or blood-sugar level meters. The devices are not limited particularly if the device is capable of measuring a state of the health in the home. The health measuring devices 10a to 10n may be devices of one type or various devices which are combined when they are used.

As shown in FIG. 10, the terminal device 20 incorporates a microprocessor 21 for controlling the terminal device 20; a ROM 30 in which BIOS or OS has been stored; a RAM 32 serving as a work area; a flash memory 34 for storing application software and data; a receiving means 50 for receiving data transmitted from each of the health measuring devices 10a to 10n; a connection terminal 52 for receiving data; a communication means 60 for performing data communication with an external terminal; a connection terminal 62 for the circuit; an LCD monitor 70; operation buttons 82, 84, 86 and 88; a voice output circuit 90 for performing voice guidance; and a speaker device 92.

The receiving circuit 100 and the receiving connection terminal 102 for receiving data transmitted from the health measuring devices 10a to 10n vary depending on the communication method of the health measuring devices 10a to 10n. A reading circuit and a connection terminal adaptable to the communication method are provided. If synchronous serial communication is employed, a receiving circuit for the synchronous serial communication and a connection terminal suitable to the foregoing method are employed. When start-stop serial communication is employed, a receiving circuit for the start-stop serial communication and connection terminal suitable to the foregoing method are employed. If the communication method is able to communicate data between the health measuring devices 10a to 10n and the terminal device 20, the communication method is not limited.

The communication means 60 and the connection terminal 62 for the circuit vary depending on the type of the communication network 30. That is, an adaptable communication circuit and a connection terminal are provided. If the public line is used, a public-line modem circuit and a connection terminal for the public line must be employed. If the CATV line is used, a cable modem circuit and a connection terminal for the CATV circuit must be provided. The communication network 30 further includes the PHS line and the ISDN line. The communication network is not limited.

The voice output circuit 90 and the speaker device 92 output voice to a user to guide the method of using the terminal device 20. Voice files included in the application software is coded to be adaptable to the state so that voice is output from the speaker device 92.

Judgment of Communication Method

In the conventional in-home health caring system, the receiving means 50 for receiving health data transmitted from each of the health measuring devices 10a to 10n and the connection terminal 52 for receiving data vary depending on the communication method of the health measuring devices 10a to 10n. Therefore, adaptable receiving means and connection terminal must be provided. If the synchronous serial communication method is used, a synchronous serial communication receiving means and a connection terminal adaptable to the synchronous serial communication method must be employed. If the start-stop serial communication method is used, a start-stop serial communication receiving means and a connection terminal adaptable to the foregoing communication must be employed. If plural types of communication methods, such as the synchronous method, asynchronous method, serial communication and another communication, are provided among the health measuring devices 10a to 10n and the terminal device 20, a user must switch the line and the terminal adaptable to the communication method whenever the health measuring devices 10a to 10n adapted to a different communication method. Therefore, a complicated operation must be performed.

Therefore, the in-home health caring system according to this embodiment has the structure that the communication is performed among the health measuring devices 10a to 10n and the terminal device 20 through a common connection terminal 52. The structure for performing the communication will now be described.

As shown in FIG. 11, the synchronous serial communication is performed such that synchronous clocks (CLK) are transmitted from the transmitting means 13a to 13n to the terminal device 20 through the terminals 14a to 14n at synchronizing intervals of 46 $\mu$m to 130 $\mu$m. At this time, data (DATA) synchronized with the synchronous clocks are transmitted.

The communication among the health measuring devices 10a to 10n and the terminal device 20 is started by emitting a data request signal (DREQ) from a first terminal 100 of the connection terminal 52 of the terminal device 20 to the health measuring devices 10a to 10n. First terminals 15a to 15n of the terminals 14a to 14n of the health measuring devices 10a to 10n receive the data request signal (DREQ). In response to the data request signal (DREQ), synchronous clocks (CLK) are transmitted from fourth terminals 18a to 18n of the terminals 14a to 14n to the terminal device 20 through third terminals 17a to 17n.

In the terminal device 20, a fourth terminal 106 and a third terminal 104 of the connection terminal 52 receive the synchronous clocks (CLK) and data (DATA). Note that a second terminal 102 of the connection terminal 52 and control means 16a to 16n are common ground terminals.

When a start-stop serial communication conforming RS232C is employed, as shown in FIG. 12, the communication between each health measuring devices 10a to 10n and the terminal device 20 is started by emitting a data request signal (DREQ) from the first terminal 100 of the connection terminal 52 of the terminal device 20 to the health measuring devices 10a to 10n. The first terminals 15a to 15n of the terminals 14a to 14n of the health measuring devices 10a to 10n receive the data request signal (DREQ). In response to the data request signal (DREQ), data (DATA) is transmitted from the third terminals 17a to 17n to the terminal device 20. In the terminal device 20, the third terminal 104 of the connection terminal 52 receives data (DATA). Note that the second terminal 102 of the connection terminal 52 and the control means 16a to 16n of the terminals 14a to 14n are common ground terminals. The fourth terminal 108 of the connection terminal 52 and the fourth terminals 18a to 18n of the terminals 14a to 14n are not used in the foregoing communication method. In FIGS. 11 and 12, a chart shows signals when viewed from the health measuring device 10a.

As described above, the in-home health caring system according to this embodiment enables data communication to be performed by using the common connection terminal 52 if health data is communicated by using a different communication method. Therefore, a user is not required to select a connection terminal to be adaptable to the communication method.

If the common terminal is employed, the received signal must be assigned in the terminal device 20 in order to enable the terminal device 20 to receive health data from the health measuring devices 10a to 10n. Then, a data receiving application adaptable to the communication method must be constituted so as to be selected by the user. Then, input of data is permitted. Therefore, a very complicated process is required.

Therefore, as shown in FIG. 13, the terminal device 20 is structured such that received data is branched to transmit data of the synchronous serial communication to a port 112 of the microprocessor 21. Data of the start-stop serial communication is transmitted to a port 114 of the microprocessor 21.

The in-home health caring system according to this embodiment has a delay time from receipt of the data request signal (DREQ) from the terminal device 20 to transmission of data, as shown in FIG. 14, the delay time being provided for each communication method of the health measuring devices 10a to 10n. An individual delay time is set for each communication method. For example, 100 ms is provided for the start-stop serial communication, while 500 ms is provided for the synchronous serial communication. Note that the number of the delay times is not limited to the foregoing values. The number may be changed to be adaptable to the employed communication methods.

The process of the receiving means 50 corresponding to the determining means of the terminal device 20 which is performed at the foregoing time will now be described. The receipt of the start-stop serial communication is waited for with a width of 50 ms to 150 ms, while the receipt of the synchronous serial communication is waited for with a width of 400 ms to 600 ms.

The terminal device 20 waits for data of the start-stop serial communication. If data is transmitted within a period of time from 50 ms to 150 ms from start of the waiting, a determination is performed that the communication method is the start-stop serial communication. Then, a process of data is performed. After a lapse of 150 ms, data of the synchronous serial communication is waited for. If data is transmitted in a period of time of 400 ms to 600 ms from start of the waiting, a determination is made that the communication method is the synchronous serial communication. Then, a process of data is performed. If data is transmitted until a 50 ms elapses from start of the waiting, if data is transmitted in a period of time from 150 ms to 400 ms or if no data is transmitted after a lapse of 600 ms, an error in the data communication is determined. The foregoing fact is communicated to the user.

The in-home health caring system according to this embodiment has the delay time for each communication method. Therefore, if the health measuring devices 10a to 10n having individual communication methods are employed, the user does not recognize the communication method. By simply connecting the communication cable to the common terminal to transmit data, the terminal device is able to automatically determine the communication method to process data.

Detecting Wired Communication

The receiving means 50 for receiving health data transmitted from each of the health measuring devices 10a to 10n and the connection terminal 52 for receiving data vary depending on the communication method of the health measuring devices 10a to 10n. Therefore, adaptable receiving means and connection terminal must be provided. If the synchronous serial communication method is used, a synchronous serial communication receiving means and a connection terminal adaptable to the synchronous serial communication method must be employed. If the start-stop serial communication method is used, a start-stop serial communication receiving means and a connection terminal adaptable to the foregoing communication must be employed. As a matter of course, any reading means and a connection terminal may be provided if the communication between the health measuring devices 10a to 10n and the terminal device 20 is permitted.

A communication cable 100 for connecting the health measuring devices 10a to 10n and the terminal device 20 has a schematic structure as shown in FIG. 15. The data receiving connection terminal 52 of the terminal device 20 is a plug 120 (see FIG. 16) adaptable to a probe 110 of the communication cable 100. A detecting switch 140 for detecting the reliable connection between the plug 120 and the probe 110 is disposed at an end of the plug 120 (see FIG. 17). The detecting switch 140 has a projection 141 which is capable of downwards moving the leading end of the probe 110. When the probe 110 has completely be inserted into the plug 120 as shown in FIG. 18, the projection 141 is downwards moved. Thus, the detecting switch 140 is switched on so that the complete connection is detected.

When the health measuring devices 10a to 10n and the terminal device 20 have been connected to one another by the communication cable 100, the connection shown in FIG. 19 is established. That is, the first terminal 15, the second terminal 16 and the third terminal 17 constituting the connection terminals 14a to 14n of the health measuring devices 10a to 10n are connected to a first terminal 121, a second terminal 122 and a third terminal 123, which constitute the plug 120 of the terminal device 20. The connections are established through a first terminal 111 and a second terminal 112 and a third terminal 113 of the probe 110, which are provided for the end of the communication cable 100, and the signal lines 171, 172 and 173.

When the probe 110 has completely be inserted into the plug 120, the detecting switch 140 is switched on. Thus, a signal indicating this is transmitted to the microprocessor 21. Thus, the microprocessor 21 transmits, to the health measuring devices 10a to 10n, a request signal for transmission of data, the signal being transmitted through the signal line 171. The health measuring devices 10a to 10n, which have received the request signal, transmit measured data to the terminal device 20 through the signal line 173. Note that the signal line 172 is a ground line in this embodiment.

In the in-home health caring system according to this embodiment, a user is required to simply connect the communication cable 100 between the health measuring devices 10a to 10n and the terminal device 20. Thus, communication of health data can automatically be started. Therefore, the complicated operation required for the conventional structure to input health data can be omitted. Note that a detecting means may be provided for each of the health measuring devices 10a to 10n to detect the connection between the health measuring devices 10a to 10n and the communication cable 100. Thus, transmission of data is started.

In the above-mentioned structure, the detecting switch 140 serving as the detecting means is not provided between the health measuring devices 10a to 10n and the communication cable 100. Therefore, the health measuring devices 10a to 10n and the communication cable 100 must initially be connected to one another. Also a detecting switch 141 may be provided for each of the connection terminals 14a to 14n of the health measuring devices 10a to 10n. To communicate a state of the detecting switch 141 provided for the health measuring devices 10a to 10n, a fourth terminal 114 is provided to the probe 110 of the communication cable 100, as shown in FIG. 20. As shown in FIG. 21, a signal line 174 is provided between each of the health measuring devices 10a to 10n and the terminal device 20.

The foregoing structure enables the terminal device 20 to determine whether or not the communication cable 100 has been connected to the health measuring devices 10a to 10n. Therefore, communication of data can automatically be started after a confirmation of the reliable connection of the two ends of the communication cable 100.

As an alternative to the foregoing detecting means (the detecting switches 140 and 141), a detecting means for detecting whether or not the wired communication can electrically be performed may be provided. That is, as shown in FIG. 22, a signal line 174 is added to the structure shown in FIG. 19. Thus, a fourth terminal 18 of the health measuring devices 10a to 10n to which the signal line 174 is grounded. In the foregoing structure, the receiving means 50 to which the signal line 174 is connected pulls up the signal line 174 in the terminal device 20.

When the communication cable 100 is not connected (see FIG. 23(a), as shown in FIG. 23, the structure is arranged such that the receiving means 50 pulls up the signal level to cause the signal level to be "H (High)". Therefore, when the health measuring devices 10a to 10n and the terminal device 20 are not connected to one another by the signal line 174, the signal level of a port 210 of the microprocessor 21 of the terminal device 20 is made to be "H". After the connection has been established, the signal level of the port 210 is made to be "L (Low)".

In the foregoing structure, the signal level of the port 210 of the microprocessor 21 is changed when the connection among the health measuring devices 10a to 10n and the terminal device 20 have been established to permit communication regardless of the connecting order of the health measuring devices 10a to 10n and the terminal device 20. Therefore, detection of the change enables communication of data to automatically be started.

A structure which is capable of obtaining the foregoing effect without addition of the signal line 174 will now be described. As shown in FIG. 24, a detecting means 19 is provided for the receiving means 50 of the terminal device 20 to detect the signal level of the signal line 171. Moreover, a detecting means 190 is provided for the storage means 12a to 12n of the health measuring devices 10a to 10n. Thus, when the health measuring devices 10a to 10n and the terminal device 20 are connected to one another and thus communication has been permitted, the signal level of the signal line 171 is changed. The detecting means 190 incorporates a switch 192 and a voltage-level detecting circuit 196.

The operation of the foregoing structure will now be described. When the health measuring devices 10a to 10n and the terminal device 20 are not connected to one another, the switch 192 serving as the detecting means is switched off, as shown in FIG. 24. Therefore, the signal level of the port 216 of the microprocessor 21 is "H". When the health measuring devices 10a to 10n and the terminal device 20 have been connected to one another, the detecting means 19 lowers the signal level of the signal line 171 to "L", as shown in FIG. 25. Thus, the signal level of the port 216 of the microprocessor 21 is made to be "LOW". As a result, completion of the connection can be detected. After the completion of the connection has been detected, the switch 192 is switched on, as shown in FIG. 26. Thus, communication of data is started.

When the communication cable 100 for the wired communication is connected, specifically, when the probe 110 is inserted into the plug 120, noise is produced in the signal lines 171 and so forth, as shown in FIG. 27. Produced noise sometimes causes a malfunction because noise is introduced into the signal line for transmitting data or the signal line for performing control. Therefore, the terminal device 20 is structured such that a signal supplied to the signal line 171 and so forth is interrupted from point A (see FIG. 27) at which completion of the connection has been confirmed to lapse of waiting time T. Thus, an influence of noise can be prevented. When communication of data is started at point B (see FIG. 27), resistance against noise which is produced owning to contact between the probe 110 and the plug 120 can be improved.

As shown in FIG. 28, switches 242, 244 (and 246) are provided for the signal lines in the terminal device 20 to which the signal lines 171, 172, 173 (and 174) are connected. The switches 242, 244 (and 246) are switched off until the connection has been confirmed. Thus, the connection is physically interrupted. After the connection of the signal lines 171, 172, 173 (and 174) has been confirmed, the switches 242, 244 (and 246) are switched on to start communication of data. As a result of the foregoing structure, an influence of noise which is produced when the signal lines 171, 172, 173 (and 174) are connected can completely be eliminated.

As described above, the embodiment of the present invention has the structure that when wired communication is permitted, communication of data from the health measuring devices 10a to 10n to the terminal device 20 is automatically started. Therefore, a necessity of performing a process for depressing a transmission button or the like can be eliminated. As a result, input of health data is facilitated. When, a plurality of health measuring devices are employed, information about the health measuring device with which the wired communication will be performed must be input to the terminal device 20.

Therefore, an ID code particular to each health measuring devices 10a to 10n may be added to measured data which must be transmitted.

In a case of a sphygmomanometer, ID code "01" of the sphygmomanometer is transmitted, and then data of the measured blood pressure is transmitted. In a case of a clinical thermometer, ID code "02" of the clinical thermometer is transmitted, and then data of the measured body temperature is transmitted. The ID code of each device is artificially and previously set by so as to be stored in the transmitting means 13a to 13n of the health measuring devices 10a to 10n.

In the terminal device 20, the microprocessor 21 determines the transmitted ID code so as to automatically recognize the health measuring device from which measured data has been transmitted. Moreover, a calculating process, a display process, a storage process and so forth corresponding to measured data are performed. As a result, a necessity of previously inputting, to the terminal device 20, information about the health measuring device with which wired communication will be performed can be eliminated. As a result, input of health data to the terminal device 20 can furthermore easily be performed.

Communication Control

The data transferring device 50, as shown in FIG. 29, incorporates a receiving circuit 54 for receiving health data transmitted from the health measuring devices 10a to 10n; a connection terminal 55 for receiving data; a transmitting circuit 56 for wireless-transmitting received health data to the terminal device 20; a light transmitting device 57 for transmitting data; and a control device 52 for controlling the foregoing devices.

Communication of data between the terminal device 20 and the data transferring device 50 is performed by using infrared-ray communication. Therefore, the connection terminal 102 and the light transmitting device 57 are provided. The wireless communication includes a multiplicity of methods as well as the infrared-ray communication. If the method is able to perform communication of data, the method is not limited.

The specifications of the infrared-ray communication which are employed in this embodiment will now be described. The following specification is an example, and the specification is not limited to this.

As a carrier wave, an infrared ray having a wavelength band of 900 nm to 950 nm is employed. The frequency band for a sub-carrier wave is 36.7±0.3 kHz and the duty ratio is 33%. In this embodiment, the pulse train is subjected to PPM (Pulse Phase Modulation). The amplitude of the sub-carrier wave is modulated (subjected to primary modulation) with the pulse train. The sub-carrier wave is used to modulate the amplitude of the infrared ray. The modulation method is arranged as described above. A waveform of the thus-formed basic signal is shown in FIG. 6. Note that time T is basic signal time and T=436 μs. Time t is sub-carrier wave (having a frequency of 36.7 kHz and a duty ratio of 33%).

As a data format for the communication, a format shown in FIG. 31 is employed. In FIG. 31, leader is a marker indicating the leading end of the signal and HD is a header code. The header code HD is able to contain information about the manufacturer codes of the health measuring devices 10a to 10n and codes indicating the types of the health measuring devices 10a to 10n. Therefore, interference with a device which employs another infrared-ray communication can be prevented. DATA is a portion for holding health data measured by the health measuring devices 10a to 10n. P is a parity code which is a 4-bit code for verifying an error or transmitted data. The parity code P is a value obtained by sectioning header code HD and health data DATA into four-bit portions and by obtaining the exclusive OR of the foregoing portions. Verification of an error using the parity code is performed by comparing the parity code P received by the terminal device 20, the header code HD and parity code P' obtained by re-calculation from health data DATA with one another. Trailer is a marker indicating the trailing end of the signal.

The terminal device 20 according to this embodiment, as shown in FIG. 32, incorporates a communication control device 22 for controlling wired communication which is performed with the health measuring devices 10a to 10n and wireless communication which is performed with the data transferring device 50. The communication control device 22 has a function of performing an interruption process. A priority order of interruption is previously provided to wait for receipt of data transmitted from the health measuring devices 10a to 10n and the data transferring device 50. The communication control device 22 according to this embodiment waits for data (data which is transmitted by the wireless communication) which is transmitted from the data transferring device 50 with priority. During wireless communication between the data transferring device 50 and the microprocessor 21 or when the health measuring devices 10a to 10n (which employs the wired communication) and the data transferring device 50 (which employs the wireless communication) have simultaneously started communication, the communication control device 22 performs a mask process to prevent interruption of the wired communication from the health measuring devices 10a to 10n. When data has been transmitted from the data transferring device 50 during wired communication from the health measuring devices 10a to 10n to the terminal device 20, the communication from the health measuring devices 10a to 10n is stopped. In this case, data transmitted from the data transferring device 50 is received with priority. The reason why data transmitted by the wireless communication with priority as compared with the wired communication is that a process for requiring re-transmission of data transmitted by the wired communication can easily be performed as compared with data transmitted by the wireless communication. As a matter of course, data which is given the priority is not limited to this.

As a result, in the in-home health caring system according to this embodiment, the terminal device 20 performs the interruption process of the wired communication from the health measuring devices 10a to 10n and the wireless communication from the data transferring device 50. Therefore, data of either of the methods can reliably be received.

In the in-home health caring system according to this embodiment, when wireless communication is interrupted during wired communication or when wired communication and wireless communication are simultaneously performed, completion of the wireless communication is waited for. Then, the wired communication is continued. After the wireless communication has been completed, the communication control device 22 requests the health measuring devices 10a to 10n, which have been again connected, to transmit data. As a result, both of the data items can be received.

Since the communication control device 22 masks interruption of the wired communication, there is a possibility that data which is communicated by the wired communication cannot be received by the terminal device 20 when wired communication is performed during wireless communication. Therefore, a structure may be employed in which an interruption signal from the receiving circuit for receiving data from the health measuring devices 10a to 10n is detected so as to hold information about the interruption signal. An interruption detecting means 120 having a function for erasing the held information item may be added. As a result, if wired communication is performed during wireless communication, execution of the wired communication can be recognized. Therefore, after the wireless communication has been completed, transmission of data can be requested to the health measuring devices 10a to 10n which has performed the wired communication.

The communication control device 22 checks information which is held by the interruption detecting means 120 after receipt of data transmitted by the wireless communication. If information indicating interruption is detected, information in the interruption detecting means 120 is erased. Then, the communication control device 22 requests the health measuring devices 10a to 10n to transmit data. Therefore, a state in which wired communication which is performed during wireless communication cannot be received by the terminal device 20 can be prevented.

To enable the in-home health caring system to prevent the state in which data communicated by the wired communication cannot be received by the terminal device 20 if wired communication is performed during wireless communication, a cable for connecting the health measuring devices 10a to 10n and the terminal device 20 must be connected until the wired communication is completed. That is, if the cable of the health measuring devices 10a to 10n which perform the wired communication during the wireless communication is removed, the request to transmit data cannot be performed. Therefore, the foregoing structure cannot overcome the above-mentioned state.

Therefore, a structure may be employed in which data can simultaneously be received without the request for transmission if wired communication and wireless communication are simultaneously performed or if either communication is performed during another communication.

For example, as shown in FIG. 34, communication control devices 24 and 26 each having a buffer function for storing data are connected to the receiving circuit 100 and the receiving circuit 110 for receiving data from the data transferring device 50. The communication control devices 24 and 26 are able to independently store data. Thus, after all of the data items have been received, the communication control devices 24 and 26 transfer data to the microprocessor 21.

If the microprocessor 21 is in a state in which it is able to perform the wired communication and the wireless communication, the microprocessor 21 may receive data transmitted by either of the communication method. If data is transmitted by another communication method during the foregoing receiving process, the microprocessor 21 may operate the communication control devices 24 and 26.

The present invention is not limited by these embodiments.

In the embodiment, although the several specific features are in the same device of the present invention, only one feature could be employed.

As described above, according to the aspect of the present invention, the system incorporates the plural health measuring devices each having the means for measuring a state of the health and the means for transmitting measured data to the data transferring device thereof; the data transferring device incorporating the means for reading data transmitted by the health measuring device and means for wireless-transmitting, to the terminal device, read data; and the operation means incorporating the means for receiving data wireless-transmitted by the data transferring means, the means for managing data and the means arranged to be operated by a user. Therefore, only one of the data transferring device capable of reading data of all of the health measuring devices enables a necessity of providing means for performing wireless transmission for all the health measuring devices to be eliminated. Therefore, data measured by the health measuring device can be wireless-transmitted to the terminal device. As a result, an effect can be obtained in that the low-cost in-home health caring system which can easily be operated is provided.

According to the aspect of the present invention, the data transferring means has the structure according to the in-home health caring system claimed in claim 1, wherein there is provided the means for identifying a user, and ID data of the person identified by the means for identifying a user is enabled to be transmitted to the terminal device. Therefore, an effect can be obtained in that the in-home health caring system is provided with which data of each person can be input to the terminal device from a remote position if a plurality of user use the system and which can easily be operated.

According to another aspect of the present invention, the data transferring means has the structure according to the in-home health caring system described above, wherein there is provided the means for remote-controlling the terminal device, and the control code for remote-controlling the terminal device is enabled to be transmitted to the terminal device. Therefore, the data transferring device is able to remote-control the terminal device. Therefore, all of the operations of the terminal device can be performed from a remote position. As a result, an effect can be obtained in that the in-home health caring system is provided which can easily be operated.

According to another aspect of the present invention, there is provided the in-home health caring system comprising: the plural health measuring devices each having the means for measuring a state of the health and the means for transmitting measured data to the data transferring device; the data transferring device incorporating the means for reading data transmitted by the health measuring device and the means for wireless-transmitting, to the terminal device, read data; and the terminal device incorporating the means for receiving data wireless-transmitted by the data transferring device, the means for managing data and the means arranged to be operated by a user, wherein the data transferring device is provided with the means for inputting numerals, characters and graphics, and data input by the input means is enabled to be transmitted to the terminal device. Therefore, provision of one data transferring device which is capable of reading data of the health measuring device enables the necessity of providing means having the wireless transmission function for all of the health measuring device to be eliminated. Data measured by the health measuring device can be wireless-transmitted to the terminal device. Data which cannot be read by the data transferring device can be input to the data transferring device by using the means for inputting numerals, characters and graphics. As a result, an effect can be obtained in that the low-cost in-home health caring system is provided which can easily be operated and with which data of the health measuring device which cannot be read by the data transferring device can be input to the terminal device.

Another aspect of the present invention, there is provided an in-home health caring system comprising: a plurality of health measuring devices each having means for measuring a state of the health and means for transmitting measured data to a data transferring device; the data transferring device incorporating means for reading data transmitted by the health measuring device and means for wireless-transmitting, to a terminal device, read data; and the terminal device incorporating means for receiving data wireless-transmitted by the data transferring device, means for managing data and means arranged to be operated by a user, further comprising an input device having means for inputting numerals, characters and graphics and means for wireless-transmitting supplied data to the terminal device. Therefore, provision of one data transferring device which is capable of reading data of the health measuring device enables the necessity of providing the means capable of performing wireless transmission for all of the health measuring devices to be eliminated. Therefore, data measured by the health measuring device can be wireless-transmitted to the terminal device. Data of the health measuring device which cannot be read by the data transferring device can be wireless-transmitted to the terminal device by using the input device. Therefore, an effect can be obtained in that the low-cost in-home health caring system which can easily be operated and with which data of the health measuring device which cannot be read by the data transferring device can be input to the terminal device.

Another aspect of the present invention, there is provided the in-home health caring system comprising: the health measuring device incorporating the measuring means for measuring a state of the health and the transmitting means for transmitting measured data to the terminal device; and the terminal device incorporating the receiving means for receiving data transmitted by the health measuring device and the managing means for managing received data, wherein one connection terminal and the determining means for determining a communication method of data received through the connection terminal are provided for the terminal device so that data transmitted from the health measuring device by using a variety of communication methods is received by the terminal device through the connection terminal. Therefore, the use is not required to select the connection terminal adaptable to the communication method. Therefore, the connection of the health measuring device can correctly be established. Moreover, the communication method of the health measuring device can automatically be determined/processed by the terminal device. Therefore, an effect can be obtained in that the in-home health caring system can be provided with which a user does not recognize the communication method if a variety of communication methods are employed to perform data communication between the health measuring device and the terminal device when health data is communicated between the health measuring device and the terminal device.

In a structure according to the in-home health caring system of the present invention described above, wherein the health measuring device is arranged to transmit data after a lapse of a delay time previously determined for each communication method after the health measuring device and the terminal device have been connected to each other, and the determining means for determining the communication method of the terminal device measures time taken from establishment of the connection between the health measuring device and the terminal device to start of transmission of data to determine the communication method employed by the health measuring device. Therefore, the communication method can be determined only by measuring time from the establishment of the connection between the health measuring device and the terminal device to start of transmission of data. As a result, an effect can be obtained in that the communication method can easily and accurately be determined.

As described above, according to an aspect of the present invention, there is provided the in-home health caring system comprising: the health measuring device incorporating the measuring means for measuring a state of health and the transmitting means for transmitting measured data to the terminal device; and the terminal device incorporating the receiving means for receiving data transmitted from the health measuring device and structured such that wired communication is performed between the health measuring device and the terminal device, wherein the detecting means for detecting whether or not the wired communication is enabled is provided for at least either of the health measuring device or the terminal device, and transmission of data from the health measuring device to the terminal device is started when detection has been made that the wired communication can be performed. Therefore, the necessity of performing the operation for starting communication of health data after the wired communication has been enabled can be eliminated. Since transmission of health data is automatically started after the wired communication has been enabled, the in-home health caring system can be provided with which a complicated operation for inputting health data to the terminal device is not required.

In a structure of the in-home health caring system of the present invention described above, wherein the detecting means incorporates a circuit portion in which the logical level of a signal is inverted when the wired connection between the health measuring device and the terminal device permits communication. Therefore, whether or not the wired communication can be performed can electrically be detected. Therefore, an effect can be obtained in that the state in which the communication can be permitted can reliably be detected.

In a structure of the in-home health caring system of the present invention described above, wherein data is transmitted from the health measuring device after a lapse of a predetermined waiting time from detection of the communication permissible state by the detecting means. Therefore, transmission of data is not performed in a period of time in which noise is most easily produced. The foregoing period of time is made to be the waiting time. Therefore, a malfunction caused from noise produced when the health measuring device and the terminal device are connected to each other can be prevented. Therefore, an effect can be obtained in that the reliability of communication of data can be improved.

In a structure of the in-home health caring system of the present invention described above, wherein the signal line disposed between the health measuring device and the terminal device to transmit data is physically interrupted until the waiting time elapses. Therefore, noise produced when the health measuring device and the terminal device are connected to each other can be interrupted. As a result, an effect can be obtained in that a malfunction caused from noise can be prevented.

Another aspect of the present invention, there is provided the in-home health caring system comprising: the health measuring device incorporating the measuring means for measuring a state of health and the transmitting means for transmitting data to the terminal device; and the terminal device incorporating the receiving means for receiving data transmitted from the health measuring device and the managing means for managing received data, wherein the communication control portion for performing an interruption process is provided for the terminal device, and the communication control portion performs waiting for receipt of data transmitted by wired communication or wireless communication. Therefore, if the interruption process causes both of the wired communication and the wireless communication to simultaneously be performed or if transmission of data by either communication method is started during receipt of data by another method, the communication method which has been previously set is received with priority. Therefore, a possibility of generation of data which cannot be received can be lowered. As a result, an effect can be obtained in that the in-home health caring system can be provided with which health data can easily be input to the terminal device.

In a structure according to the in-home health caring system of the present invention, when data transmitted by the wireless communication has been received during receipt of data by the wired communication, the communication control portion of the terminal device interrupts the receipt of data by the wired communication and data transmitted by the wireless communication is received with a priority, and then data transmitted by the wired communication is received. Therefore, both of data items transmitted by the wired communication and the wireless communication can be received. Therefore, an effect can be obtained in that operability of a process for inputting health data to the terminal device and the reliability of the system can be improved.

In a structure according to the in-home health caring system of the present invention, wherein when data transmitted by the wired communication is received during receipt of data transmitted by the wireless communication, the communication control portion of the terminal device does not interrupt receipt of data transmitted by the wireless communication and receives data transmitted by the wireless communication with a priority, and then the communication control portion receives data transmitted by the wired communication. Therefore, data transmitted by both of the wired communication and the wireless c can be received. Thus, an effect can be obtained in that the operability of the process for inputting health data to the terminal device and the reliability of the system can be improved.

According to another aspect of the present invention, there is provided an in-home health caring system comprising: a health measuring device incorporating measuring means for measuring a state of health and transmitting means for transmitting measured data to a terminal device; and a terminal device incorporates receiving means for receiving data transmitted by the health measuring device and managing means for managing received data, wherein a communication control portion having a buffer function is provided for the terminal device, and when data transmitted by wireless communication or wired communication is received during receipt of data by the other communication method which is the wireless communication or the wired communication, the communication control portion temporarily stores data transmitted by the other communication method until receipt of data transmitted by the communication method which has previously been employed is completed. Therefore, both of data items transmitted by the wired communication and the wireless communication can be received. As a result, an effect can be obtained in that health data can easily be input to the terminal device by a user.

What is claimed is:

1. A health care communication system comprising:
   a transmitting device transmitting health care data, located outside of a health care facility;
   a receiving device located in said health care facility, said receiving device having receiving means for receiving data transmitted by said transmitting device and managing means for managing received data;
   detecting means for detecting whether or not communication of data by wire between said transmitting device and said receiving device is permitted, said detecting means being provided with at least one of said transmitting device and said receiving device,
   wherein when said detecting means detects a fact that communication of data is permitted, said transmitting device starts transmitting data to said receiving device.

2. A health care communication system according to claim 1, wherein said receiving device includes a communication-method determining portion, said communication-method determining portion is arranged to determine the communication method of received data to decide a method of processing data in accordance with determined communication method.

3. A health care communication system according to claim 1, wherein said transmitting device includes a relay device for wireless-transmitting read data to said receiving device said relay device having reading means for reading data which is transmitted by said transmitting device to said receiving device and, said receiving device includes means for receiving wireless-transmitted data by said relay device.

4. A health care communication system according to claim 1, said receiving device includes a communication control portion for performing an interruption process so that said communication control portion waits for receipt of data transmitted by said transmitting device by communication.

5. A health-care communication system comprising:
  a health measuring device that measures an individual's state of health, located outside a health care facility, and transmits measured data;
  a terminal, located in said health care facility, that receives the measured data transmitted by the health measuring device and manages the received data;
  a detector provided on at least one of either the health measuring device or the terminal, wherein the detector detects whether communication of data by wire between the health measuring device and the terminal can be accomplished, and
  wherein the health measuring device automatically starts transmitting the measured data in response to the detector detecting that communication between the health measuring device and the terminal can be accomplished.

6. A communication system according to claim 5, wherein said detector applies a predetermined voltage to a signal line of a communication line arranged to communicate data between the health measuring device and the terminal and connected to one of said health measuring device and said terminal and, wherein the signal line, when also connected to the other one of the health measuring device is grounded so that the detector detects a change in the logical level of the signal line which occurs when connection of the communication line is established between said health measuring device and said terminal.

7. A communication system according to claim 5, wherein said health measuring device adds to the data to be transmitted a particular identification code for identifying said health measuring device, and wherein said terminal recognizes the identification code transmitted from said health measuring device to decide a method of processing the data which has been transmitted together with the identification code in accordance with the identification code.

8. A communication system according to claim 5, said terminal performing an interruption process to wait for receipt of data transmitted by said health measuring device.

9. A communication system according to claim 5, wherein said terminal includes a communication control portion having a buffer function, and when said communication control portion has received data from the health measuring device transmitted by one of wireless communication and wired communication during receipt of data transmitted by the other communication method, said communication control portion temporarily stores data transmitted by the one communication method until receipt of data transmitted by the other communication method is completed.

10. A communication system according to claim 5, wherein said health measuring device starts transmitting data to said terminal after a predetermined waiting time has elapsed since the detector detected that communication between the health measuring device and the terminal is permitted.

11. A communication system according to claim 10, wherein a signal line for transmitting data between said health measuring device and said terminal is physically interrupted until the waiting time elapses.

12. A communication system according to claim 5, wherein said terminal is configured to determine a communication method by which the data was transmitted to select a method of processing the data in accordance with the determined communication method.

13. A communication system according to claim 12, wherein said health measuring device transmits data after a delay time has elapsed since establishment of a connection between said health measuring device and said terminal, wherein the delay time is determined for the communication method, and wherein the terminal is configured to measure time since establishment of the connection between said health measuring device and said terminal to the start of transmission of the data so as to determine the communication method employed by said health measuring device.

14. A communication system according to claim 5, wherein when said terminal receives data transmitted by wireless communication during receipt of data transmitted by wired communication, said terminal interrupts the receipt of data transmitted by the wired communication, and subsequently receives data transmitted by wired communication after the data transmitted by the wireless communication has been received.

15. A communication system according to claim 14, wherein when said terminal receives data transmitted by wired communication during receipt of data transmitted by wireless communication, said terminal continues receipt of data transmitted by wireless communication, and subsequently receives data transmitted by wired communication after the data transmitted by wireless communication has been received.

16. A communication system according to claim 5, wherein said health measuring device includes a relay device for wireless-transmitting data to said terminal, wherein said relay device is capable of reading data transmitted by said health measuring device to said terminal and, said terminal is capable of receiving the wireless-transmitted data by said relay device.

17. A communication system according to claim 16, wherein said relay device can identify a user and transmit identification data particular to the identified user, and wherein said terminal processes data for each user identified in accordance with the identification data.

18. A communication system according to claim 17, wherein said relay device transmits a control code for controlling said terminal.

19. A communication system according to claim 17, wherein said relay device has a first input for entering data for transmission to said terminal.

20. A communication system according to claim 17, wherein the relay device includes an auxiliary input for manually entering data and a wireless-transmitter for transmitting input data to said terminal by wireless communications.

21. A method of providing health-care data, the method comprising:
  measuring an individual's state of health with a health measuring device at a location outside a health care facility;
  detecting whether communication of data by wire between the health measuring device and a terminal, located at said health care facility, for managing the measured data can be accomplished;
  automatically starting to transmit the measured data from the health measuring device to the terminal after it is determined that communication between the health measuring device and the terminal can be accomplished.

22. A method according to claim 21 wherein the act of detecting includes:
  applying a predetermined voltage to a signal line of a communication line arranged to communicate data between the health measuring device and the terminal and connected to one of said health measuring device and said terminal; and detecting a change in the logical level of the signal line which occurs when connection of the communication line is established between the health measuring device and the terminal.

23. A method according to claim 21 including:

adding to the data to be transmitted from the health measuring device a particular identification code for identifying the health measuring device;

recognizing the identification code when received by the terminal; and deciding a method of processing the data which has been transmitted together with the identification code based on the identification code.

24. A method according to claim 21 including transmitting the data to the terminal by wireless communication.

25. A method according to claim 21 including:

receiving data in the terminal transmitted by wireless communication during receipt of data transmitted by wired communication;

interrupting the receipt of data transmitted by the wired communication; and subsequently receiving, in the terminal, the data transmitted by wired communication after the data transmitted by the wireless communication has been received.

26. A method according to claim 21 including:

receiving, in the terminal, data transmitted by wired communication during receipt of data transmitted by wireless communication;

continuing to receive, in the terminal, the data transmitted by wireless communication; and subsequently receiving, in the terminal, the data transmitted by wired communication after the data transmitted by wireless communication has been received.

27. A method according to claim 21 including:

receiving, in the terminal, data from the health measuring device transmitted by one of either wireless or wired communication during receipt of data transmitted by the other communication method; and temporarily storing data transmitted by the one communication method until receipt of data transmitted by the other communication method is completed.

28. A method according to claim 21 including starting to transmit data from the health measuring device to the terminal after a predetermined waiting time has elapsed since the detecting that communication between the health measuring device and the terminal can be accomplished.

29. A method according to claim 28 including physically interrupting a signal line for transmitting data between the health measuring device and the terminal until the waiting time elapses.

30. A method according to claim 21 including:

determining a communication method by which the data was transmitted; and selecting a method of processing the data in accordance with the determined communication method.

31. A method to claim 30 including:

transmitting data from the health measuring device after a delay time has elapsed since establishment of a connection between the health measuring device and the terminal, wherein the delay time is determined for the communication method;

measuring the time elapsed since establishment of the connection between the health measuring device and the terminal until the start of transmission of the data; and determining the communication method employed by the health measuring device based on the elapsed time.

32. A method according to claim 21 including:

identifying a user and transmitting identification data particular to the identified user; and processing data for each user identified based on the identification data.

33. A method according to claim 32 including transmitting a control code for controlling the terminal remotely.

34. A method according to claim 32 including manually entering data for transmission to the terminal.

35. A health-care communication system comprising:

a health measuring device that measures an individual's state of health and transmits measured data;

a terminal that receives the measured data transmitted by the health measuring device and manages the received data;

a detector provided on at least one of either the health measuring device or the terminal, wherein the detector detects whether communication of data by wire between the health measuring device and the terminal can be accomplished;

wherein the health measuring device automatically starts transmitting the measured data in response to the detector detecting that communication between the health measuring device and the terminal can be accomplished;

wherein said detector applies a predetermined voltage to a signal line of a communication line arranged to communicate data between the health measuring device and the terminal and connected to one of said health measuring device and said terminal; and wherein the signal line, when also connected to the other one of the health measuring device is grounded so that the detector detects a change in the logical level of the signal line which occurs when connection of the communication line is established between said health measuring device and said terminal.

36. A health-care communication system comprising:

a health measuring device that measures an individual's state of health and transmits measured data;

a terminal that receives the measured data transmitted by the health measuring device and manages the received data;

a detector provided on at least one of either the health measuring device or the terminal, wherein the detector detects whether communication of data by wire between the health measuring device and the terminal can be accomplished;

wherein the health measuring device automatically starts transmitting the measured data in response to the detector detecting that communication between the health measuring device and the terminal can be accomplished; and wherein said health measuring device starts transmitting data to said terminal after a predetermined waiting time has elapsed since the detector detected that communication between the health measuring device and the terminal is permitted.

37. A communication system according to claim 36, wherein a signal line for transmitting data between said health measuring device and said terminal is physically interrupted until the waiting time elapses.

38. A health-care communication system comprising:
a health measuring device that measures an individual's state of health and transmits measured data;
a terminal that receives the measured data transmitted by the health measuring device and manages the received data;
a detector provided on at least one of either the health measuring device or the terminal, wherein the detector detects whether communication of data by wire between the health measuring device and the terminal can be accomplished;
wherein the health measuring device automatically starts transmitting the measured data in response to the detector detecting that communication between the health measuring device and the terminal can be accomplished;
wherein said health measuring device adds to the data to be transmitted a particular identification code for identifying said health measuring device; and
wherein said terminal recognizes the identification code transmitted from said health measuring device to decide a method of processing the data which has been transmitted together with the identification code in accordance with the identification code.

39. A health-care communication system comprising:
a health measuring device that measures an individual's state of health and transmits measured data;
a terminal that receives the measured data transmitted by the health measuring device and manages the received data;
a detector provided on at least one of either the health measuring device or the terminal, wherein the detector detects whether communication of data by wire between the health measuring device and the terminal can be accomplished;
wherein the health measuring device automatically starts transmitting the measured data in response to the detector detecting that communication between the health measuring device and the terminal can be accomplished;
wherein said terminal is configured to determine a communication method by which the data was transmitted to select a method of processing the data in accordance with the determined communication method;
wherein said health measuring device transmits data after a delay time has elapsed since establishment of a connection between said health measuring device and said terminal, wherein the delay time is determined for the communication method; and
wherein the terminal is configured to measure time since establishment of the connection between said health measuring device and said terminal to the start of transmission of the data so as to determine the communication method employed by said health measuring device.

40. A health-care communication system comprising:
a health measuring device that measures an individual's state of health and transmits measured data;
a terminal that receives the measured data transmitted by the health measuring device and manages the received data;
a detector provided on at least one of either the health measuring device or the terminal, wherein the detector detects whether communication of data by wire between the health measuring device and the terminal can be accomplished;
wherein the health measuring device automatically starts transmitting the measured data in response to the detector detecting that communication between the health measuring device and the terminal can be accomplished;
wherein when said terminal receives data transmitted by wireless communication during receipt of data transmitted by wired communication, said terminal interrupts the receipt of data transmitted by the wired communication, and subsequently receives data transmitted by wired communication after the data transmitted by the wireless communication has been received; and
wherein when said terminal receives data transmitted by wired communication during receipt of data transmitted by wireless communication, said terminal continues receipt of data transmitted by wireless communication, and subsequently receives data transmitted by wired communication after the data transmitted by wireless communication has been received.

41. A health-care communication system comprising:
a health measuring device that measures an individual's state of health and transmits measured data;
a terminal that receives the measured data transmitted by the health measuring device and manages the received data;
a detector provided on at least one of either the health measuring device or the terminal, wherein the detector detects whether communication of data by wire between the health measuring device and the terminal can be accomplished;
wherein the health measuring device automatically starts transmitting the measured data in response to the detector detecting that communication between the health measuring device and the terminal can be accomplished; and
wherein said terminal includes a communication control portion having a buffer function, and when said communication control portion has received data from the health measuring device transmitted by one of wireless communication and wired communication during receipt of data transmitted by the other communication method, said communication control portion temporarily stores data transmitted by the one communication method until receipt of data transmitted by the other communication method is completed.

42. A method of providing health-care data, the method comprising:
measuring an individual's state of health with a health measuring device;
detecting whether communication of data between the health measuring device and a terminal for managing the measured data can be accomplished;
automatically starting to transmit the measured data from the health measuring device to the terminal after it is determined that communication by wire between the health measuring device and the terminal can be accomplished;
wherein the act of detecting includes:
applying a predetermined voltage to a signal line of a communication line arranged to communicate data between the health measuring device and the terminal and connected to one of said health measuring device and said terminal; and detecting a change in the logical level of the signal line which occurs when connection of the communication line is established between the health measuring device and the terminal.

43. A method of providing health-care data, the method comprising:

measuring an individual's state of health with a health measuring device;

detecting whether communication of data between the health measuring device and a terminal for managing the measured data can be accomplished;

automatically starting to transmit the measured data from the health measuring device to the terminal after it is determined that communication by wire between the health measuring device and the terminal can be accomplished;

determining a communication method by which the data was transmitted;

selecting a method of processing the data in accordance with the determined communication method;

transmitting data from the health measuring device after a delay time has elapsed since establishment of a connection between the health measuring device and the terminal, wherein the delay time is determined for the communication method;

measuring the time elapsed since establishment of the connection between the health measuring device and the terminal until the start of transmission of the data; and determining the communication method employed by the health measuring device based on the elapsed time.

44. A method of providing health-care data, the method comprising:

measuring an individual's state of health with a health measuring device;

detecting whether communication of data between the health measuring device and a terminal for managing the measured data can be accomplished;

automatically starting to transmit the measured data from the health measuring device to the terminal after it is determined that communication by wire between the health measuring device and the terminal can be accomplished;

receiving data in the terminal transmitted by wireless communication during receipt of data transmitted by wired communication;

interrupting the receipt of data transmitted by the wired communication; and subsequently receiving, in the terminal, the data transmitted by wired communication after the data transmitted by the wireless communication has been received.

45. A method of providing health-care data, the method comprising:

measuring an individual's state of health with a health measuring device;

detecting whether communication of data between the health measuring device and a terminal for managing the measured data can be accomplished;

automatically starting to transmit the measured data from the health measuring device to the terminal after it is determined that communication by wire between the health measuring device and the terminal can be accomplished;

receiving, in the terminal, data transmitted by wired communication during receipt of data transmitted by wireless communication;

continuing to receive, in the terminal, the data transmitted by wireless communication; and subsequently receiving, in the terminal, the data transmitted by wired communication after the data transmitted by wireless communication has been received.

46. A method of providing health-care data, the method comprising:

measuring an individual's state of health with a health measuring device;

detecting whether communication of data between the health measuring device and a terminal for managing the measured data can be accomplished;

automatically starting to transmit the measured data from the health measuring device to the terminal after it is determined that communication by wire between the health measuring device and the terminal can be accomplished;

receiving, in the terminal, data from the health measuring device transmitted by one of either wireless or wired communication during receipt of data transmitted by the other communication method; and temporarily storing data transmitted by the one communication method until receipt of data transmitted by the other communication method is completed.

* * * * *